United States Patent
Yen

(10) Patent No.: US 10,201,530 B2
(45) Date of Patent: *Feb. 12, 2019

(54) TREATMENT OF BRCA1-DEFECTIVE CANCER OR RESISTANT CANCERS

(71) Applicant: City of Hope, Duarte, CA (US)

(72) Inventor: Yun Yen, Arcadia, CA (US)

(73) Assignee: City of Hope, Duarte, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/900,677

(22) Filed: Feb. 20, 2018

(65) Prior Publication Data

US 2018/0185338 A1 Jul. 5, 2018

Related U.S. Application Data

(63) Continuation of application No. 15/242,249, filed on Aug. 19, 2016, now Pat. No. 9,931,322, which is a continuation of application No. PCT/US2015/022809, filed on Mar. 26, 2015.

(60) Provisional application No. 61/970,737, filed on Mar. 26, 2014.

(51) Int. Cl.
| | |
|---|---|
| *A61K 31/426* | (2006.01) |
| *A61K 33/24* | (2006.01) |
| *A61K 31/7068* | (2006.01) |
| *A61K 45/06* | (2006.01) |
| *A61K 31/337* | (2006.01) |

(52) U.S. Cl.
CPC .......... *A61K 31/426* (2013.01); *A61K 31/337* (2013.01); *A61K 31/7068* (2013.01); *A61K 33/24* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 4,177,263 A | 12/1979 | Rosenberg et al. | |
| 4,584,316 A | 4/1986 | Rosenberg et al. | |
| 4,861,760 A | 8/1989 | Mazuel et al. | |
| 4,911,920 A | 3/1990 | Jani et al. | |
| 5,212,162 A | 5/1993 | Missel et al. | |
| 5,399,694 A | 3/1995 | Riess et al. | |
| 5,403,841 A | 4/1995 | Lang et al. | |
| 5,648,362 A | 7/1997 | Riess et al. | |
| 7,956,076 B2 * | 6/2011 | Yen ..................... | C07D 277/46 514/371 |
| 8,163,783 B2 | 4/2012 | Yen et al. | |
| 8,372,983 B2 | 2/2013 | Yen et al. | |
| 9,931,322 B2 | 4/2018 | Yen | |
| 2009/0258915 A1 | 10/2009 | Yen et al. | |
| 2010/0272717 A1 | 10/2010 | Evans et al. | |
| 2011/0245304 A1 | 10/2011 | Yen et al. | |
| 2012/0253048 A1 | 10/2012 | Yen et al. | |

FOREIGN PATENT DOCUMENTS

WO WO-2013/116765 A1 8/2013

OTHER PUBLICATIONS

Al-Muhammed, J. et al. (May-Jun. 1996). "In-vivo studies on dexamethasone sodium phosphate liposomes," *J Microencapsul* 13(3):293-306.
Cheung-Ong, K. et al. (May 23, 2013). "DNA-damaging agents in cancer chemotherapy: serendipity and chemical biology," *Chem Biol* 20(5):648-659.
Chonn, A. et al. (Dec. 1995). "Recent advances in liposomal drug-delivery systems," *Curr Opin Biotechnol* 6(6):698-708.
Eyles, J.E. et al. (Jul. 1997). "Oral delivery and fate of poly(lactic acid) microsphere-encapsulated interferon in rats," *J. Pharm. Pharmacol.* 49(7):669-674.
Friedeson, B. (Aug. 6, 2007). "The BRCA1/2 pathway prevents hematologic cancers in addition to breast and ovarian cancers," *BMC Cancer* 7:152.
Gao, Z.H. et al. (Jun. 1995). "Controlled release of a contraceptive steroid from biodegradable and injectable gel formulations: in vitro evaluation," *Pharm. Res.* 12(6):857-863.
International Search Report dated Jun. 26, 2015, for PCT Application No. PCT/US2015/022809, filed Mar. 26, 2015, 3 pages.
Li, M. et al. (May 13, 2013). "Function of BRCA1 in the DNA damage response is mediated by ADP-ribosylation," *Cancer Cell* 23(5):693-704.
Lin, Z.P. et al. (Mar. 2014, e-published Jan. 10, 2014). "Triapine disrupts CtIP-mediated homologous recombination repair and sensitizes ovarian cancer cells to PARP and topoisomerase inhibitors," *Mol Cancer Res* 12(3):381-303.
Ostro, M.J. et al. (Aug. 1989). "Use of liposomes as injectable-drug delivery systems," *Am J Hosp Pharm* 46(8):1576-1587.
Rao, K.P. (1995). "Recent developments of collagen-based materials for medical applications and drug delivery systems," *J. Biomater Sci. Polym. Ed.* 7(7):623-645.
Written Opinion dated Jun. 26, 2015, for PCT Application No. PCT/US2015/022809, filed Mar. 26, 2015, 4 pages.
Zhou, B. et al. (Nov. 2013, e-published Sep. 26, 2013). "A small-molecule blocking ribonucleotide reductase holoenzyme formation inhibits cancer cell growth and overcomes drug resistance," Cancer Res 73(21):6484-6493.

* cited by examiner

*Primary Examiner* — Kamal A Saeed
(74) *Attorney, Agent, or Firm* — Mintz

(57) ABSTRACT

Provided herein are methods of treating cancer in a subject by administering COH29 ((N-(4-(3,4-dihydroxyphenyl)-5-phenylthiazol-2-yl)-3,4-dihydroxybenzamide)). The methods of treating include treating a BRCA1-defective subject, a PARP1 inhibitor-resistant subject or a DNA-damaging anti-cancer agent resistant subject. The methods include treating cancer by administering COH29 and a DNA-damaging anti-cancer agent in a combined synergistic amount.

16 Claims, 13 Drawing Sheets

Specification includes a Sequence Listing.

SEQUENCE LISTING

<160> NUMBER OF SEQ ID NOS: 4

<210> SEQ ID NO 1
<211> LENGTH: 19
<212> TYPE: RNA
<213> ORGANISM: Artificial sequence
<220> FEATURE:
<223> OTHER INFORMATION: Synthetic polynucleotide

<400> SEQUENCE: 1
ucacaguguc cuuuaugua                                                  19

<210> SEQ ID NO 2
<211> LENGTH: 19
<212> TYPE: RNA
<213> ORGANISM: Artificial sequence
<220> FEATURE:
<223> OTHER INFORMATION: Synthetic polynucleotide

<400> SEQUENCE: 2
uacauaaagg acacuguga                                                  19

<210> SEQ ID NO 3
<211> LENGTH: 24
<212> TYPE: DNA
<213> ORGANISM: Artificial sequence
<220> FEATURE:
<223> OTHER INFORMATION: Synthetic polynucleotide

<400> SEQUENCE: 3
aggaattgcg ggaggaaaat gggt                                            24

<210> SEQ ID NO 4
<211> LENGTH: 24
<212> TYPE: DNA
<213> ORGANISM: Artificial sequence
<220> FEATURE:
<223> OTHER INFORMATION: Synthetic polynucleotide

<400> SEQUENCE: 4 gcccctgaa gatctttctg tcct                                             24

TREATMENT OF BRCA1-DEFECTIVE CANCER OR RESISTANT CANCERS

CROSS-REFERENCES TO RELATED APPLICATIONS

This application is a continuation application of U.S. Non-provisional application Ser. No. 15/242,249, filed Aug. 19, 2016, which is a continuation application of PCT Application No. PCT/US2015/022809, filed Mar. 26, 2015, which claims the benefit of priority under 35 U.S.C. § 119(e) of U.S. Provisional Application No. 61/970,737, filed Mar. 26, 2014. The disclosure of each of the prior applications is considered part of and is incorporated by reference in the disclosure of this application.

STATEMENT AS TO RIGHTS TO INVENTIONS MADE UNDER FEDERALLY SPONSORED RESEARCH AND DEVELOPMENT

This invention was made with government support under grant number CA 127541, awarded by the National Institute of Cancer (NCI) and grant number P30CA033572 awarded by the National Institutes of Health (NIH). The government has certain rights in this invention.

REFERENCE TO A "SEQUENCE LISTING," A TABLE, OR A COMPUTER PROGRAM LISTING APPENDIX SUBMITTED AS AN ASCII FILE

The Sequence Listing written in file 048440-541C02US_ST25.TXT, created on Feb. 20, 2018, 1,143 bytes, machine format IBM-PC, MS-Windows operating system, is hereby incorporated by reference.

BACKGROUND OF THE INVENTION

The antimetabolite drug hydroxyurea (HU) has been used to treat a variety of human cancers including chronic myelogenous leukemia, head and neck, cancer, and others (1). Its primary anticancer target is ribonucleotide reductase (RR), which reduces ribonucleotides to their corresponding deoxy forms to supply dNTPs for DNA replication and repair (3,4). The human RR is composed of the hRRM1 and hRRM2 submits (3,4). Following a genotoxic stimuli an alternate RR enzyme is induced to supply dNTPs for DNA repair, which is composed of hRRM1 and p53R2 (a homologue of hRRM2 transactivated by the tumor suppressor protein p53) (5). Within cells, HU is known to inhibit both types of RR(4) through generating free radicals via oxidative transformation (6) that quenches free-radical mediated catalysis (3). However, pharmacologically, HU therapy suffers from short half-life in vivo and problematic side effects, most notably myelosuppression, aid gastrointestinal and dermatologic effects (7).

Poly(ADP-ribose) polymerase-1 (PARP1) and PARP2 are both ADP-ribosyl transferases (ART) with roles in tumor development. ART members with PARP activity such as PARP1 contain a conserved catalytic domain with a highly conserved active site sequence (12-14). Following single strand DNA breaks PARP1 synthesizes ADP-ribose polymers from β-NAD+ substrate and transfers these to glutamate, lysine or aspartate residues of acceptor proteins (itself or other proteins), which are subsequently degraded by poly(ADP-ribose) glycohydrolase (PARG). During single strand DNA break repair (SSBR) or base-excision repair (BER), PARP1 and PARP2 interact with X-ray repair complementing protein-1 (XRCC1) to recruit SSBR/BER factors, DNA polymerase β or DNA ligase III to the site of DNA damage (12-14). Without PARP1, the continuing presence of single strand breaks during DNA replication will lead to stalled replication forks, whose resolution require BRCA1 or BRCA2-mediated homologous repair (HR) (15, 16). BRCA1 along with BRCA2 are tumor suppressor genes linked to the onset of familial breast cancers (11) In the absence of BRCA1, double strand breaks consequently accumulate, resulting in cell death via apoptosis. BRCA1/2-defective tumors may be sensitive to PARP1 inhibitors but can suffer from acquired resistance to PARP1 inhibitors. Thus, there is a need in the art for BRCA1/2-defective tumor treatments that avoid side effects and/or acquired resistance associated with current therapies. Accordingly, provided herein are solutions to these and other problems in the art.

BRIEF SUMMARY OF THE INVENTION

Disclosed herein, inter alia, are methods of treating cancer in a BRCA1 defective subject a PARP1 inhibitor-resistant subject, or a DNA-damaging anti-cancer agent resistant subject, by administering an effective amount of COH29 (including pharmaceutically acceptable salts thereof). Also disclosed are methods of treating cancer in a subject by administering COH29 (including pharmaceutically acceptable salts thereof) and a DNA-damaging anti-cancer agent in a combined synergistic amount.

BRIEF DESCRIPTION OF THE DRAWINGS

FIG. 1A: Dose response curves for ovarian cancer cells expressing wt (wild-type) BRCA1 (OV90) or mutant BRCA1 (UWB1.289) incubated with COH29 for 72 h, and lysed (Cell viability was assessed by MIT assay) and the points depicted represent an average of three independent experiments with error bars indicated; growth of tumor explants established with HCC1937 (FIG. 1B) and HCC1937+BRCA1.

FIG. 3A): The effect of COH29 on PARP1 activity in isogenic pairs of breast (HCC1937) and ovarian (UWB1.289) cancer cell lines expressing mutant or wt BRCA1 (wt=+BRCA1 in each case) was assessed in duplicate using procedures described in *Materials & Methods*; FIG. 3B: The effect of COH29 on PARP1 protein expression in the isogenic HCC1937/HCC1937+BRCA1 cell lines was assessed by Western blot analysis using anti-human PARP1 antibody as the primary antibody. Loading control is β-actin.

FIG. 4A: Viability of HCC1937 and HCC1937+BRCA1 cells treated with a fixed concentration of COH29 (12.5 µM) plus cisplatin (12.5, 25, 50 and 100 µM) for 24 h assessed by MTT assay (the points depicted represent an average of three independent experiments with error bars indicated);

FIG. 4B: Histogram of 24 h viability in the cells indicated in the presence of 5 μM COH29 alone, 4 μM cisplatin alone, or the combination of the two drugs at the same concentrations (Shown are the averages of three independent experiments).

FIG. 5A: Wild-type zebrafish embryos at 4 dpf (day post-fertilization) exposed to HU as indicated (morphological changes in the eye and heart development are indicated by the arrowheads). FIG. 5B: Bar graph of the effect of a series of different concentrations of HU on zebrafish (0, 5, 10, 20, 30 mM, n=50, performed in triplicate). FIG. 5C: Wild-type zebrafish embryos at 4 dpf exposed to COH29 as indicated. FIG. 5D: Bar graph of the effect of a series of different concentrations of COH29 on zebrafish (0, 10, 20, 50, 100 μM, n=46, performed in triplicate).

FIG. 7A: The effect of COH29 on DDR-associated proteins were assessed in cytoplasm and nucleus by Western blot analysis, where cells were treated with COH29 at the indicated doses for 48 h and cell lysates were subjected to immunoblotting using the indicated antibodies (FOXO3 activity is indicated by the levels of its downstream, target p27Kip1 and β-Tubulin and Lamin A/C represent the fractionation and loading controls of Cyt, and Nuc Extracts); FIGS. 7B-7D: The effect of COH29 on colonization of DDR-related proteins, phospho-ATM (FIG. 7B), γ-H2AX. (FIG. 7C), and phospho-p53 (FIG. 7D) and foxo3 in the nucleus was assessed by indirect immunofluorescence assay. For each protein an average of 300 of the stained cells was analyzed and a histogram shows the percentage (%) of cells with positive nuclei (≥2.5 foci) where the number of biological replicates is three, the error bars represent standard deviation (SD) and P values (paired t-test) are as indicated).

FIG. 9A: The effect of COH29 on RAD51 protein was assessed by indirect immunofluorescence assay using anti-human RAD51 antibody as the primary antibody. FIG. 9B: The effect of COH29 on RAD51 protein was assessed by Western blot analysis using anti-human RAD51 antibody as the primary antibody (loading control was β-actin), for the analysis: A549 lung cancer cells were treated with COH29 at the indicated doses for 24 h and the expression pattern of γ-H2AX following the COH-29 treatment was also similarly analyzed in FIGS. 9A and 9B.

DETAILED DESCRIPTION OF THE INVENTION

Definitions

Figure 1A:
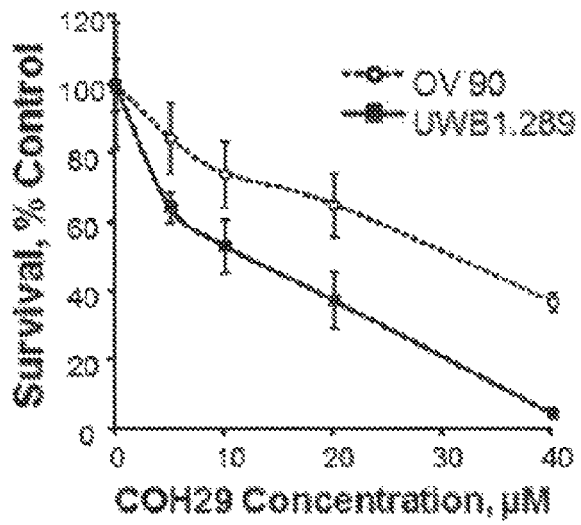
FIGS. 1A-1B. BRCA1 status affects COH29 cytotoxicity and antitumor activity.

"Patient," "subject" "patient in need thereof," and "subject in need thereof" are herein used interchangeably and refer to a living organism suffering from or prone to a disease or condition that can be treated by administration of a COH29 or COH29 in combination with other anti-cancer agents as discussed herein. In embodiments, the disease or condition is cancer. Non-limiting examples of subjects include humans, other mammals, bovines, rate, mice, dogs, monkeys, goat sheep, cows, deer, and other non-mammalian animals. In embodiments, a patient is human.

A "cancer subject" as used herein refers to a subject who has a cancer as described herein. A cancer subject may have at least one of the cancers described herein. Thus, for example, a cancer subject may refer to a "breast cancer subject" (e.g. a subject having breast cancer) or an "ovarian cancer subject" (e.g. a subject having ovarian cancer). Cancer subjects may have cancers that exhibit specific genotypic or phenotypic characteristics (e.g. defective gene products or resistance to specific anti-cancer agents). Accordingly, a cancer subject may be a "BRCA1-defective subject" where a BRCA1-defective subject is a subject who has a cancer that includes a BRCA1 defective gene or BRCA1 defective protein (e.g. a "BRCA1-defect"). In embodiments, a "BRCA1-defective subject" refers to the non-expression (e.g. reduced expression relative to control or healthy subjects) of the BRCA1 gene, absence of (e.g. reduced amount relative to control or healthy subjects) functional BRCA1 in the subject or reduced expression of a BRCA1 that causes, at least in part, directly or indirectly, cancer in the subject. In embodiments, a BRCA1-defective subject displays non-expression of the BRCA1 gene, absence of functional BRCA1 in the subject. A cancer subject may be a "PARP1 inhibitor-resistant subject" where a PARP1 inhibitor-resistant subject is a subject who has a cancer resistant to at least one PARP1 inhibitor as known in the art. A cancer subject may be a "DNA-damaging anti-cancer agent resistant subject" where such a subject has a cancer resistant to at least one DNA-damaging anti-cancer agent as known in the art. Cancer subjects may have cancers that exhibit more than one genotypic or phenotypic characteristic (e.g. a breast cancer subject may have a cancer that has a BRCA1-defect and resistance to at least one PARP1 inhibitor).

"COH29" refers to a compound having formula (N-(4-(3,4-dihydroxyphenyl)-5-phenylthiazole-2yl)-2-yl)-3,4-dihydroxybenzamide):

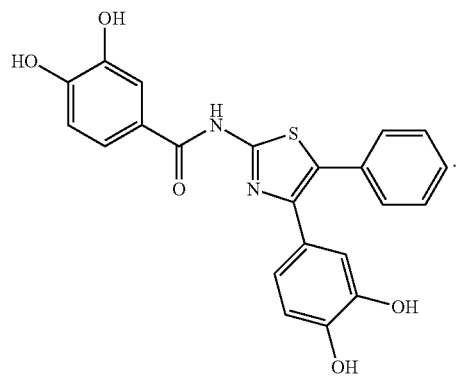

(COH29)

COH29 and its synthesis are described in U.S. Pat. Nos. 7,956,076; 8,372,983, and International Application No.: PCT/US13/24490 which are herein incorporated in their entirety.

COH29 may be administered to cancer subjects described herein, including for example, a breast cancer subject, an ovarian cancer subject, a BRCA1-defective subject, a PARP1 inhibitor-resistant subject or a DNA-damaging anti-cancer agent resistant subject. The administration may be at a therapeutically effective amount as set forth herein.

"BRCA1" is used according to its common, ordinary meaning and refers to proteins of the same or similar names and functional fragments and homologs thereof. The term includes recombinant or naturally occurring forms of BRCA1 (e.g. breast cancer 1, early onset; GI No: 1698399), or variants thereof that maintain BRCA1 activity (e.g. within at least 30%, 40%, 50%, 60%, 70%, 80%, 90%, 95%, or 100% activity compared to BRCA1).

"γ-H2AX" is used according to its common, ordinary meaning and refers to proteins of the same or similar names and functional fragments and homologs thereof. The term includes any recombinant or naturally occurring form of γ-H2AX (e.g. γhistone H2AX; GI No: 4504253), or variants thereof that maintain γ-H2AX activity (e.g. within at least 30%, 40%, 50%, 60%, 70%, 80%, 90%, 95%, or 100% activity compared to γ-H2AX).

"Rad51" is used according to its common, ordinary meaning and refers to proteins of the same or similar names and functional fragments and homologs thereof. The term includes any recombinant or naturally occurring form of Rad51 (e.g. GI No: 49168602), or variants thereof that maintain Rad51 activity (e.g. within at least 30%, 40%, 50%, 60%, 70%, 80%, 90%, 95%, or 100% activity compared to Rad51).

"PAR1" is used according to its common, ordinary meaning and refers to proteins of the same or similar names and functional fragments and homology thereof. The term includes any recombinant or naturally occurring form of PARP1 (e.g. poly [ADP-ribose] polymerase 1; GI No: 156523968), or variants thereof that maintain PARP1 activity (e.g. within at least 30%, 40%, 50%, 60%, 70% 80%, 90%, 95%, or 100% activity compared to PARP1). A "PARP1 inhibitor" is a composition (e.g. compound, peptide, protein, nucleic acid, or antibody) which inhibits the activity of PARP1 (NAD$^+$ ADP-ribosyltransferase 1).

"PARP1 inhibitors" are compositions (e.g. a compound, polypeptide, amino acid, polynucleotide, nucleic acid, or antibody) effective at treating cancers by inhibiting the activity of, or the expression of PARP1. Non-limiting examples of PARP1 inhibitors include olaparib, veliparib, iniparib, and niraparib.

"DNA-damaging anti-cancer agents" are compositions (e.g. a compound, polypeptide, amino acid, polynucleotide, nucleic acid, or antibody) effective at treating cancers by damaging DNA. DNA-damaging anti-cancer agents can be chemotherapeutic. In embodiments, DNA-damaging agents include irradiation (e.g. γ-irradiation). The interaction of a DNA-damaging anti-cancer agent may be direct (e.g. binding or interacting with DNA itself) or indirect (e.g. binding or interacting with other molecules interacting with DNA). Herein, DNA-damaging anti-cancer agents include, for example, alkylating agents (e.g. ethylenimines, methylmelamines, nitrosoureas, nitrogen mustards, busulfans, cyclophosphamides, and procarbazines), antimetabolites, anthracyclines, platinum based agents, taxanes, kinase inhibitors, histone deacetylase inhibitors (HDAC), topoisomerase inhibitors, and nucleotide analogues. In embodiments, DNA-damaging anti-cancer agents include compositions that intercalate between DNA base pairs or bind in the minor or major grooves of a DNA. In embodiments, the DNA-damaging anti-cancer agents is a Topoisomerase I agent, camptothecin, irinotecan, topotecan, a Topoisomerase II agent, cisplatin, carboplatin, oxaliplatin, adriamycin (e.g., doxorubicin), etoposide, a single-strand break agent (e.g. BCNU (carmustine), CCNU (lomustine)), DTIC (dacarbazine), cytoxan (cyclophosphamide), ifosfamide, bleomycin, and mitomycin C.

"Chemotherapeutic" or "chemotherapeutic agent" is used in accordance with its plain ordinary meaning and refers to a chemical composition or compound having antineoplastic properties or the ability to inhibit the growth or proliferation of cells.

The anticancer drug cisplatin has been used to treat various human cancers including, for example, ovarian cancer, testicular cancer, germ cell tumors, small cell lung cancer, lymphomas, head and neck cancer, and bladder cancer. Herein, a "platinum-based compound" or "platinum containing agent" as refers to a compound comprising a heavy metal complex containing a central atom of platinum surrounded by organic and/or inorganic functionalities. Included within platinum-based compounds are platinum-based drugs. Non-limiting examples of platinum-based compounds include, cisplatin, carboplatin, nedaplatin, oxaliplatin, satraplatin, triplatin, tetranitrate, pharmaceutically acceptable salts thereof, stereoisomers thereof, derivatives thereof, analogues thereof, and combinations thereof. The term "cisplatin" includes derivatives and analogues such as those described in U.S. Pat. Nos. 4,177,263, 4,584,316, 5,648,362 and 5,399,694, which are herein incorporated by reference in their entirety.

Cisplatin anticancer activity stems primarily from the crosslinking of DNA in target cells, which requires an exchange reaction involving cisplatin chloride ions with nucleophile groups. Cisplatin causes bidentate lesions in DNA through formation of intrastrand adducts with d(GpG) or d(ApG) sequences. Cisplatin is also capable of generating interstrand crosslinks, which can interfere with DNA replication. The lessons activate the DNA damage checkpoint, resulting in the arrest of cell cycle progression. The formation of secondary tumors in patients represents one of the major issues associated with cisplatin therapy. Other side effects of cisplatin may include nephrotoxicity, neurotoxicity, nausea, ototoxicity, myelotoxicity, and electrolyte imbalance. Cisplatin resistance is also found in cancer patients.

The terms "treating" or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof include prevention of an injury, pathology, condition, or disease.

As used herein, the term "cancer" refers to all types of cancer, neoplasm, malignant or benign tumors found in mammals, including leukemia, carcinomas and sarcomas. Exemplary cancers include breast cancer, ovarian cancer, colon cancer, liver cancer, kidney cancer and pancreatic cancer. Additional examples include leukemia (e.g. acute myeloid leukemia ("AML") or chronic myelogenous leukemia ("CML")), cancer of the brain, lung cancer, non-small cell lung cancer, melanoma, sarcomas, and prostate cancer, cervix cancers, stomach cancers, head & neck cancers, uterus cancers, mesothelioma, metastatic bone cancer, medulloblastoma, Hodgkin's Disease, Non-Hodgkin's Lymphoma, multiple myeloma, neuroblastoma, rhabdomyosarcoma, primary thrombocytosis, primary macroglobulinemia, primary brain tumors, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine and exocrine pancreas.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved, myeloid (myelogenous), lymphoid (lymphogenous), or monocytic; and (3) the increase or non-increase in the number abnormal cells in the blood-leukemic or aleukemic (subleukemic). The murine leukemia model is widely accepted as being predictive of in vivo anti-leukemic activity. It is believed that a compound that tests positive in the P388 cell assay will generally exhibit some level of anti-leukemic activity regardless of the type of leukemia being treated. Accordingly, the present invention includes a method of treating leukemia, including treating acute myeloid leukemia, chronic lymphocytic leukemia acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia megakaryocyte leukemia, micromyeloblastic leukemia, monocytic leukemia, myeloblasts leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, and undifferentiated cell leukemia.

The term "sarcoma" generally refers to a tumor which is made up of a substance like the embryonic connective tissue and is generally composed of closely packed cells embedded in a fibrillar or homogeneous substance. Sarcomas which can be treated with a combination of antineoplastic thiol-binding mitochondrial oxidant and an anticancer agent include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma botryoid sarcoma, chloroma sarcoma, chorio carcinoma, embryonal sarcoma Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" is taken to mean a tumor arising from the melanocyte system of the skin and other organs. Melanomas which can be treated with a combination of antineoplastic thiol-binding mitochondrial oxidant and an anticancer agent include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant, melanoma, nodular melanoma, subungal melanoma, and superficial spreading melanoma.

The term "carcinoma" refers to a malignant new growth made up of epithelial cells tending to infiltrate the surrounding tissues and give rise to metastases. Exemplary carcinomas which can be treated with a combination of antineoplastic thiol-binding mitochondrial oxidant and an anticancer agent include, for example, acinar carcinoma, acinous carcinoma, adenocystic carcinoma, adenoid cystic carcinoma, carcinoma adenomatosum carcinoma of adrenal cortex, alveolar carcinoma, alveolar cell carcinoma, basal cell carcinoma, carcinoma basocellulare, basaloid carcinoma, basosquamous cell carcinoma bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical, cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatinfomi carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticular, lipomatous carcinoma, lymphoepithalial carcinoma, carcinoma medullars, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma, ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, selanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma, tuberosum, tuberous carcinoma, verrucous carcinoma, and carcinoma villosum.

"Cancer model organisms" are organisms (e.g. cancer cell lines) exhibiting a phenotype indicative of cancer or the activity of cancer causing elements, within the organism. The cancer model organism may exhibit a phenotype of a cancer as described herein. Accordingly, a cancer model organism may be, for example, a cancer cell line deficient in BRCA1 that is resistant to a PARP1 inhibitor, or is resistant to a DNA-damaging anti-cancer agent. A wide variety of organisms may serve as cancer model organisms, and include for example, cancer cells and mammalian organisms such as rodents (e.g. mouse or rat) and primates (such as humans). Cancer cell lines are widely understood by those skilled in the art as cells exhibiting phenotypes or genotypes similar to in vivo cancers. Cancer cell lines as used herein include cell lines from animals (e.g. mice) and from humans.

An "anti-cancer agent" used in accordance with its plain ordinary meaning and refers to a composition (e.g. a compound, polypeptide, amino acid, polynucleotide, nucleic acid, or antibody) having antineoplastic properties or the ability to inhibit the growth or proliferation of cells. In some embodiments, an anticancer agent is a chemotherapeutic. In some embodiments, an anti-cancer agent is an agent identified herein having utility in methods of treating cancer. In some embodiments, an anti-cancer agent is an agent approved by the FDA or similar regulatory agency of a country other than the USA, for treating cancer. Anti-cancer agents may be selective for certain cancers or certain tissues As used herein, the term "administering" means oral administration, administration as a suppository, topical contact intravenous, parenteral intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal sublingual, palatal gingival nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

By "co-administer" it is meant that a composition described herein is administered at the same time, just prior to, or just after the administration of one or more additional therapies. For example, COH29 can be administered alone or can be co-administered to the patient. Co-administration is meant to include simultaneous or sequential administration of the compound individually or in combination (mom than one compound or agent). Thus, the preparations can also be combined, when desired, with other active substances (e.g. to reduce metabolic degradation)

The compositions disclosed herein can be delivered transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions disclosed herein can also be delivered as microspheres for slow release in the body. For example, microspheres can be administered via intradermal injection of drug-containing microspheres, which slowly release subcutaneously (see Rao, *J. Biomater Sci Polym. Ed.* 7:623-645, 1995); as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). In another embodiment, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). The compositions can also be delivered as nanoparticles.

An "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of a "therapeutically effective amount" is an amount sufficient to contribute to the treatment, prevention, or reduction of a symptom or symptoms of a disease, which could also be referred to as a "therapeutically effective amount." A "reduction of" a symptom or symptoms (and grammatical equivalents of this phrase) means decreasing of the severity or frequency of the symptom(s), or elimination of the symptom(s). The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincoti, Williams & Wilkins).

The dosage and frequency (single or multiple doses) administered to a mammal can vary depending upon a variety of factors, for example, whether the mammal suffers from another disease, and its route of administration; size, age, sex, health, body weight body mass index, and diet of the recipient; nature and extent of symptoms of the disease being treated, kind of concurrent treatment, complications from the disease being treated or other health-related problems. Other therapeutic regimens or agents can be used in conjunction with the methods and compounds of Applicants' invention. Adjustment and manipulation of established dosages (e.g., frequency and duration) are well within the ability of those skilled in the art.

The therapeutically effective amounts described herein can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted fey monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to affect a beneficial therapeutic response in the patient over time. The size of the dose also will be determined by the existence, nature, and extent of any adverse side effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

As defined herein, the term "inhibition", "inhibit", "inhibiting" and the like in reference to a protein-inhibitor interaction, means negatively affecting (e.g. decreasing) the activity or function of the protein relative to the activity or function of the protein in the absence of the inhibitor. When used in reference to a inhibiting a gene, "inhibiting" means negatively affecting (e.g. decreasing) the activity or expression of the gene relative to the activity or expression of the gene in the absence of the inhibitor. In some embodiments inhibition refers to reduction of a disease or symptoms of disease. In some embodiments, inhibition refers to a redaction in the activity of a particular protein or nucleic acid target. Thus, inhibition includes, at least in part, partially or totally blocking stimulation, decreasing, preventing, or delaying activation, or inactivating, desensitizing, or down-regulating signal transduction or enzymatic activity or the amount of a protein.

The terms "synergy", "synergism", "synergistic", "combined synergistic amount", and "synergistic therapeutic effect" are used herein interchangeably and refer to a measured effect of compounds administered in combination where the measured effect is greater than the sum of the individual effects of each of the compounds administered alone.

Methods

In a first aspect is a method of treating cancer in a subject in need thereof. The method includes administering an effective amount of COH29 to the subject. The subject is a BRCA1-defective subject a PARP1 inhibitor-resistant subject or a DNA-damaging anti-cancer agent resistant subject as set forth herein. Thus, in embodiments, the subject is a BRCA1-defective subject. The subject may be a PARP1 inhibitor-resistant subject. The subject may be a DNA-damaging anti-cancer agent resistant subject in embodiments, the subject is at least one of a BRCA1-defective subject, a PARP1 inhibitor-resistant subject or a DNA-damaging anti-cancer agent resistant subject. Accordingly, the subject may be a BRCA1-defective subject and at least one of PARP1 inhibitor-resistant subject or a DNA-damaging anti-cancer agent resistant subject (i.e. the cancer has a BRCA1-defect and resistance to at least one of a PARP1 inhibitor or a DNA-damaging anti-cancer agent).

In embodiments, the subject is a breast cancer subject, ovarian cancer subject, colon cancer subject, liver cancer subject, kidney cancer subject, lung cancer subject, non-small cell lung cancer subject, brain cancer subject, prostate cancer subject, pancreatic cancer subject, melanoma subject, leukemia subject, or sarcoma subject.

The subject may be a breast cancer subject or an ovarian cancer subject. The subject may be a breast cancer subject. The subject may be an ovarian cancer subject. The subject may be a colon cancer subject. The subject may be a liver cancer subject. The subject may be a kidney cancer subject. The subject may be a lung cancer subject or a non-small cell lung cancer subject. The subject may be a brain cancer subject. The subject may be a prostate cancer subject. The subject may be a pancreatic cancer subject. The subject may be a melanoma subject. The subject may be a leukemia subject. The subject may be a sarcoma subject.

The cancer subject (e.g. breast, ovarian, lung, prostate, or pancreatic cancer subject) may also be least one of a BRCA1-defective subject, a PARP1 inhibitor-resistant subject or a DNA-damaging anti-cancer agent resistant subject. Thus in embodiments, the cancer subject is a BRCA1-defective subject. In embodiments, the cancer subject is a PARP1 inhibitor-resistant subject. In embodiments, the cancer subject is a DNA-damaging anti-cancer agent resistant subject. In embodiments, the cancer subject is a BRCA1-defective subject and a PARP1 inhibitor-resistant subject. In embodiments, the cancer subject is a PARP1 inhibitor-resistant subject and a DNA-damaging anti-cancer agent resistant subject. In embodiments, the cancer subject is a BRCA1-defective subject a PARP1 inhibitor-resistant subject and a DNA-damaging anti-cancer agent resistant subject.

Thus, in embodiments, the subject is a BRCA1-defective subject having breast cancer or ovarian cancer. The BRCA1-defective subject may have breast cancer. The BRCA1-defective subject may have ovarian cancer.

In embodiments, the subject is a PARP1 inhibitor-resistant subject having breast cancer or ovarian cancer. The PARP1 inhibitor-resistant subject may have breast cancer. The PARP1 inhibitor-resistant subject may have ovarian cancer.

In embodiments, the subject is a DNA-damaging anti-cancer agent resistant subject having a cancer characterized by resistance to at least one DNA-damaging anti-cancer agent including, but not limited to, cisplatin, carboplatin, oxaliplatin, adriamycin, mitoxantrone, VP16, CPT11, or camptothecin. In embodiments, the subject is a DNA-damaging anti-cancer agent resistant subject having breast cancer, ovarian, cancer, colon cancer, liver cancer, kidney cancer, lung cancer, non-small cell lung cancer, brain cancer, prostate cancer, pancreatic cancer, melanoma, leukemia, or sarcoma. The subject may be a DNA-damaging anti-cancer agent resistant subject having breast cancer. The subject may be a DNA-damaging anti-cancer agent resistant subject having ovarian cancer.

In embodiments, the subject is a BRCA1-defective subject and a PARP1 inhibitor-resistant subject. The subject may be a BRCA1-defective subject and a PARP1 inhibitor-resistant subject having breast cancer or ovarian cancer. The subject may be a BRCA1-defective subject and a PARP1 inhibitor-resistant subject having breast cancer. The subject may be a BRCA1-defective subject and a PARP1 inhibitor-resistant subject having ovarian cancer.

In embodiments, the subject is a BRCA1-defective subject and a DNA-damaging anti-cancer agent resistant subject. The subject may be a BRCA1-defective subject and a DNA-damaging anti-cancer agent resistant subject having breast cancer or ovarian cancer. The subject may be a BRCA1-defective subject and a DNA-damaging anticancer agent resistant subject having breast cancer. The subject may be a BRCA1-defective subject and a DNA-damaging anti-cancer agent resistant subject having ovarian cancer.

In embodiments, the subject is a PARP1 inhibitor-resistant subject and a DNA-damaging anti-cancer agent resistant subject. The subject may be a PARP1 inhibitor-resistant subject and a DNA-damaging anti-cancer agent resistant subject, having breast cancer or ovarian cancer. The subject may be a PARP1 inhibitor-resistant subject and a DNA-damaging anti-cancer agent resistant subject having breast cancer. The subject may be a PARP1 inhibitor-resistant subject and a DNA-damaging anti-cancer agent resistant subject having ovarian cancer.

In embodiments, the subject is a BRCA1-defective subject, a PARP1 inhibitor-resistant subject and a DNA-damaging anti-cancer agent resistant subject. The subject may be a BRCA1-defective subject, a PARP1 inhibitor-resistant subject and a DNA-damaging anti-cancer agent resistant subject having breast cancer or ovarian cancer. The subject may be a BRCA1-defective subject, a PARP1 inhibitor-resistant subject and a DNA-damaging anti-cancer agent resistant subject having breast cancer. The subject may be a BRCA1-defective subject, a PARP1 inhibitor-resistant subject and a DNA-damaging anti-cancer agent resistant subject having ovarian cancer.

In embodiments, the cancer subject is a breast cancer subject and at least one of a BRCA1-defective subject, a PARP1 inhibitor-resistant subject, or a DNA-damaging anti-cancer agent resistant subject. Thus in embodiments, the breast cancer subject is also a BRCA1-defective subject. In embodiments, the breast cancer subject is also a PARP1 inhibitor-resistant subject. In embodiments, the breast cancer subject is also a DNA-damaging anti-cancer agent resistant subject. The breast cancer subject may be a BRCA1-defective subject and a PARP1 inhibitor-resistant subject (e.g. The breast cancer subject has a cancer that has a BRCA1-defect and is resistant to a PARP1 inhibitor). The breast cancer subject may be a BRCA1-defective subject and a DNA-damaging anti-cancer agent resistant subject (e.g. the breast cancer subject has a cancer that has a BRCA1-defect and is resistant to a DNA-damaging anti-cancer agent). The breast cancer subject may be a PARP1 inhibitor-resistant subject and a DNA-damaging anti-cancer agent resistant subject (e.g. the breast cancer subject has a cancer that has resistant to a PARP1 inhibitor and to a DNA-damaging anti-cancer agent). The breast cancer subject may be a BRCA1-defective subject, a PARP1 inhibitor-resistant subject and a DNA-damaging anti-cancer agent resistant subject (e.g. the breast cancer subject has a cancer that has BRCA1-defect and is resistant to a PARP1 inhibitor and a DNA-damaging anti-cancer agent).

In embodiments, the cancer subject is an ovarian cancer subject and at least one of a BRCA1-defective subject, a PARP1 inhibitor-resistant subject, or a DNA-damaging anti-cancer agent resistant subject. Thus in embodiments, the ovarian cancer subject is also a BRCA1-defective subject. In embodiments, the ovarian cancer subject is also a PARP1 inhibitor-resistant subject. In embodiments, the ovarian cancer subject is also a DNA-damaging anti-cancer agent resistant subject. The ovarian cancer subject may be a BRCA1-defective subject and a PARP1 inhibitor-resistant subject, (e.g. the ovarian cancer subject has a cancer that has a BRCA1-defect and is resistant to a PARP1 inhibitor). The ovarian cancer subject may be a BRCA1-defective subject and a DNA-damaging anti-cancer agent resistant subject (e.g. the ovarian cancer subject has a cancer that has a BRCA1-defect and is resistant to a DNA-damaging anti-cancer agent). The ovarian cancer subject may be a PARP1 inhibitor-resistant subject and a DNA-damaging anti-cancer agent resistant subject (e.g. the ovarian cancer subject has a cancer that has resistant to a PARP1 inhibitor and to a DNA-damaging anti-cancer agent) The ovarian cancer subject may be a BRCA1-defective subject, a PARP1 inhibitor-resistant subject and a DNA-damaging anti-cancer agent resistant subject (e.g. the ovarian cancer subject has a cancer that has BRCA1-defect and is resistant to a PARP1 inhibitor and a DNA-damaging anticancer agent).

In embodiments, the cancer subject is a breast cancer subject ovarian cancer subject, colon cancer subject, liver cancer subject, kidney cancer subject, lung cancer subject, non-small cell lung cancer subject, brain cancer subject, prostate cancer subject, pancreatic cancer subject, melanoma subject, leukemia subject, or sarcoma subject. In embodiments, the cancer subject is a breast cancer subject or an ovarian cancer subject. In embodiments, the cancer subject is a breast cancer subject. In embodiments, the cancer subject is an ovarian cancer subject.

The subject may have a cancer as described herein, where the cancer exhibits at least one of a BRCA1-defect resistance to a PARP1 inhibitor, or resistance to a DNA-damaging anti-cancer agent. The cancer may be breast cancer, ovarian cancer, colon cancer, liver cancer, kidney cancer, lung cancer, non-small cell lung cancer, brain cancer, prostate cancer, pancreatic cancer, melanoma, leukemia, or sarcoma. The cancer may be one of the aforementioned cancers having a BRCA1-defect. The may be one of the aforementioned cancers having resistance to a PARP1 inhibitor. The cancer may be one of the aforementioned cancers having resistance to a DNA-damaging anti-cancer agent.

In embodiments, the cancer has a BRCA1-defect and at least one of resistance to a PARP1 inhibitor or a DNA-damaging anti-cancer agent. In embodiments, the cancer has resistance to a PARP1 inhibitor and has at least one of a BRCA1-defect or resistance to a DNA-damaging anti-cancer agent. In embodiments, the cancer has resistant to a DNA-damaging anti-cancer agent and has at least one of a BRCA1-defect or resistance to a PARP1 inhibitor.

The cancer may be breast cancer or ovarian cancer. The cancer may be breast cancer. The cancer may be ovarian cancer. The cancer may be colon cancer. The cancer may be liver cancer. The cancer may be kidney cancer. The cancer may be lung cancer or a non-small cell lung cancer. The cancer may be brain cancer. The cancer may be prostate cancer. The cancer may be pancreatic cancer. The cancer may be melanoma. The cancer may be leukemia. The cancer may be sarcoma.

In embodiments, the administration of COH29 lowers a specific protein's activity or expression in a cancer subject (e.g. a BRCA1-defective subject, a PARP1 inhibitor-resistant subject or a DNA-damaging anti-cancer agent resistant subject). The inhibition may result from the binding of COH-29 to a target protein which may induce the protein's degradation through proteasome recruitment. The change in protein level may, in turn, modulate the expression pattern of the corresponding gene. In embodiments, COH29, inhibits activity or expression of PARP1, Rad51 or BRCA1 in the subject. Analysis may be performed (e.g. microarray analysis) to identify genes that are differentially expressed as a result of COH29 treatment. Accordingly, administering COH29 may lower BRCA1 protein activity or expression in the subject. Administering COH29 may lower PARP1 protein activity or expression in the subject. Administering COH29 may lower Rad51 protein activity or expression in the subject. The subject may be a cancer subject as described herein, including embodiments thereof. In embodiments, the cancer subject is breast cancer subject ovarian cancer subject, colon cancer subject, liver cancer subject, kidney cancer subject, lung cancer subject, non-small cell lung cancer subject, brain cancer subject, prostate cancer subject, or pancreatic cancer subject. The cancer subject may be a breast cancer subject or an ovarian cancer subject.

In embodiments, the RNA expression profile of a COH29 treated BRCA1-defective subject may be compared with that of a COH29 treated cancer subject that is BRCA1+ (e.g. intact BRCA1). Thus in embodiments, COH29 inhibits activity or expression of a protein to a greater extent in a BRCA1-defective subject than in cancer subject that is BRCA1+. Thus, in embodiments, COH29 inhibits PARP1 to a greater extent in a BRCA1-defective subject than in a cancer subject that is BRCA1+. COH29 may inhibit Rad51 to a greater extent in a BRCA1-defective subject than in a cancer subject that is BRCA1+. In embodiments, COH29 treats the BRCA1-defective subject through synthetic lethality. The BRCA1-defective subject is as described herein, including embodiments thereof. In embodiments, the BRCA1-defective subject is also a breast cancer subject or an ovarian cancer subject.

In embodiments, the administration of COH29 lowers a specific protein's activity or expression in a cancer (e.g. a cancer that is BRCA1-defective or resistant to either or both a PARP1 inhibitor or a DNA-damaging anti-cancer agent). The inhibition may result from the binding of COH-29 to a target protein which may induce the protein's degradation through proteasome recruitment. The change in protein level may, in turn, modulate the expression pattern of the corresponding gene. In embodiments, COH29, inhibits activity or expression of PARP1, Rad51, or BRCA1 in the cancer. Analysis may be performed (e.g. microarray analysts) to identify genes that are differentially expressed as a result of COH29 treatment. Thus, administering COH29 may lower BRCA1 protein activity or expression in the cancer. Administering COH29 may lower PARP1 protein activity or expression in the cancer. Administering COH29 may lower Rad51 protein activity or expression in the cancer. The cancer may be a cancer as described herein, including embodiments thereof. In embodiments, the cancer is breast cancer, ovarian cancer, colon cancer, liver cancer, kidney cancer, lung cancer, non-small cell lung cancer, brain cancer, prostate cancer, or pancreatic cancer. The cancer may be breast cancer or ovarian cancer.

In embodiments, the RNA expression profile of a BRCA1-defective cancer treated with COH29 may be compared with that of a BRCA1+ cancer treated with COH29. Thus in embodiments, COH29 inhibits activity or expression of a protein to a greater extent in a cancer that is BRCA1-defective than in a cancer that is BRCA1+. COH29 may inhibit PARP1 to a greater extent in a cancer that is BRCA1-defective than in a cancer that is BRCA1+. COH29 may inhibit Rad51 to a greater extent in a cancer that is BRCA1-defective than in a cancer that is BRCA1+. In embodiments, COH29 treats a cancer that is BRCA1-defective through synthetic lethality. The cancer may be a cancer as described herein, including embodiments thereof. The cancer may be breast cancer or ovarian cancer.

COH29 may exhibit specificity toward BRCA1-defective human cancers through synthetic lethality. Thus, in embodiments, COH29 treats BRCA1-defective subjects, including embodiments thereof. In embodiments, synthetic lethality arises from inhibition of a second protein in the BRCA1-defective cancer. The second protein may be PARP1. The expression profile of a cancer having a BRCA1-defect may be compared to BRCA1+ cancer cells. In embodiments, COH29 decreases PARP1 activity by about 10%, 20%, 30% 35%, 40% 45%, 50%, 55%, 60%, 65%, 70%, 75% 80%, 85%, 90%, 95%, 96%, 97%, 98%, 99%, or 100% in a cancer that is BRCA1-defective. Thus in embodiments, COH29 inhibits PARP1 activity with greater efficacy in BRCA1-defective cancer cells than in BRCA1+ cancer cells, in embodiments, COH29 decreases PARP1 expression by about 5%, 10%, 15%, 20%, 25%, 30%, 40%, 50%, 60%, 70%, 80%, 90%, 95%, or 100% in a cancer that is BRCA1-defective. Thus in embodiments, COH29 inhibits PARP1 expression with greater efficacy in BRCA1-defective cancer cells than in BRCA1+ cancer cells.

The administration of COH29 may inhibit DNA repair in the subject. The administration of COH29 may inhibit base excision repair (BER) (e.g. repair of damaged DNA by, for example, correcting base lesions that arise due to oxidative, alkylation, deamination, and depurinatiation/depyrimidination on damage by removing damaged bases using specific glycosylates) The administration of COH29 may inhibit nucleotide excision repair (NER) (e.g. correcting DNA damage resulting in bulky DNA adducts such as damage resulting from UV exposure, by removing a short single stranded DNA segment). The administration of COH29 may inhibit double stranded DNA break repair in the subject (e.g. using the non-homologous end joining (NHEJ pathway), the microhomology mediated end joining (MMEJ) pathway, or by homologous recombination (HR)). The administration of COH29 may inhibit base excision repair, nucleotide excision repair or double stranded DNA break repair in the subject.

In embodiments, the genotoxic profile of COH29, and thus its ability to activate the DNA damage checkpoint and induce DNA damage, may be assessed by detecting modulated activity or expression of proteins such as, for example, ATM foxo3, γ-H2AX, p53, or Rad51.

The modulation may be an increase in activity or expression or a decrease in activity or expression of a protein. Thus in embodiments, the administration of COH29 increases γ-H2AX activity or expression in the subject. In embodiments, the administration of COH29 increases γ-H2AX activity or expression in the subject. The administration of COH29 may increase γ-H2AX activity or expression in the subject by at least 1-fold, 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, or 20-fold. The increased γ-H2AX activity or expression may indicate activation of the DNA damage checkpoint and induction of DNA damage. In embodiments, the administration of COH29 increases γ-H2AX activity or expression in a cancer as described herein, including embodiments thereof. In embodiments, the administration of COH29 increases γ-H2AX activity or expression in a cancer as described herein, including embodiments thereof. In embodiments, administration of COH29 increases γ-H2AX activity or expression in triple negative breast cancer. Accordingly, in embodiments, administering an effective amount of COH29 treats triple negative breast cancer COH29 may inhibit DNA double strand break (DSB) repair. DSBs may be repaired by, for example, homologous recombination (HR) or nonhomologous end joining (NHEJ) pathway. In embodiments, COH29 inhibits HR. In embodiments, COH29 inhibits the NHEJ pathway. The DNA damage response may be prolonged by suppressing the protein level of proteins involved in HR repair, such as for example, BRCA1 and Rad51. In embodiments, the administration of COH29 decreases Rad51 activity or expression in the subject or in a cancer. In embodiments, the administration of COH29 decreases BRCA1 activity or expression in the subject or in a cancer. In embodiments, the expression of BRCA1 or Rad51 is decreased in the subject or in a cancer. In embodiments, the expression of BRCA1 and Rad51 is decreased in the subject or in a cancer.

In another aspect is a method of treating cancer in a subject in need thereof. The method includes administering COH29 and a DNA-damaging anti-cancer agent in a combined synergistic amount. In embodiments, the subject is as described herein, including embodiments thereof. Thus, in certain embodiments, the subject is a BRCA1 defective subject or a PARP1 inhibitor-resistant subject. The subject may be a BRCA1 defective subject. The subject may be a PARP1 inhibitor-resistant subject.

The cancer may be breast cancer, ovarian cancer, colon cancer, liver cancer, kidney cancer, lung cancer, non-small cell lung cancer, brain cancer, prostate cancer, pancreatic cancer, melanoma, leukemia, or sarcoma. The cancer may be breast cancer or ovarian cancer. Thus, in embodiments, the subject is a breast cancer subject or an ovarian cancer subject. The subject may be a breast cancer subject. The subject may be an ovarian cancer subject. Subjects may also exhibit one or more phenotypes or genotypes as described herein, including embodiments thereof (e.g. a breast cancer subject may also a BRCA1 defective subject or a DNA-damaging anti-cancer agent resistant subject). In embodiments, the subject is a BRCA1-defective subject and a DNA-damaging anti-cancer agent resistant subject. Subjects may have a cancer having resistance to a DNA-damaging anti-cancer agent. The methods herein may afford treatment of cancers having resistance to at least one DNA-damaging anticancer agent by co-administering an effective amount of COH29.

In embodiments, the DNA-damaging anti-cancer agent is a chemotherapeutic DNA-damaging agent. The DNA-damaging anti-cancer agent may be an alkylating agent. The DNA-damaging anti-cancer agent may be an antimetabolite as described herein, including embodiments thereof. The DNA-damaging anti-cancer agent may be an anthracycline. The DNA-damaging anti-cancer agent, may be a platinum-based agent. The DNA-damaging anti-cancer agent may be a taxane. The DNA-damaging anti-cancer agent may be a kinase inhibitor The DNA-damaging anti-cancer agent may be a histone deacetylase inhibitor. The DNA-damaging anti-cancer agent may be a topoisomerase inhibitor. The DNA-damaging anti-cancer agent may be a nucleotide analogue. In embodiments, inhibition of cancer is synergistically increased in the presence of a DNA-damaging cancer agent and COH29.

In embodiments, the method of treating includes inhibiting at least two proteins in synthetic lethality. At least one of the proteins may be BRCA1. At least one of the proteins may be Rad51. At least one of the proteins may be PARP1. In embodiments, the inhibition of PARP1 may be in a BRCA1-defective subject. In embodiments, inhibition of PARP1 is synergistically increased in the presence of a DNA-damaging anti-cancer agent and COH29. The DNA-damaging anti-cancer agent may be gemcitabine, γ-irradiation, or cisplatin, including its derivatives as set forth herein.

The DNA-damaging anti-cancer agent may be cisplatin including its derivatives as described herein. In embodiments, the administration of COH29 increases the cytotoxicity of cisplatin to a level greater than the cytotoxicity of cisplatin when administered alone (e.g. administering COH29 and a cisplatin together in a combined synergistic amount). Cisplatin is a widely used chemotherapeutic whose anticancer activity is mainly attributed to DNA crosslinking in target cells. Thus, in embodiments, the co-administration of COH29 and cisplatin results in a reduction in survivability of cancer cells greater than the reduction in survivability of the cancer cells when either COH29 or cisplatin is administered alone (e.g. administering COH29 and a cisplatin together in a combined synergistic amount).

The DNA-damaging anti-cancer agent may be gemcitabine. In embodiments, the co-administration of COH29 and gemcitabine results in a reduction in survivability of cancer cells greater than the reduction in survivability of the cancer cells when either COH29 or gemcitabine is administered alone (e.g. administering COH29 and a gemcitabine together in a combined synergistic amount). The DNA-damaging anti-cancer agent may be γ-irradiation. In embodiments, the administration of COH29 and treatment with γ-irradiation results in a reduction in survivability of cancer cells greater than the reduction in survivability of the cancer cells when either COH29 or γ-irradiation is administered alone. COH29 may be administered before, during, or after treatment with γ-irradiation.

EXAMPLES

The efficacy of DNA-damaging drugs is highly influenced and modulated by cellular DNA repair capacity (9). Indeed, small-molecule inhibitors of DNA repair have been combined with conventional chemotherapy drugs in preclinical studies (18), indicating that the DNA repair machinery is a promising target for novel cancer treatments. Further, PARP inhibitors have been combined with platinum chemotherapy in clinical trials (19,20). Consistent with these reports, it was discovered, inter alia, that COH29 enhances the sensitivity of cells to cisplatin, especially in BRCA1-deficient cells. This suggests that COH29 synthetic lethality is dependent on NER or BER in HR-deficient cells. We therefore propose, without being bound by any particular theory, that COH29 interference with several DNA repair pathways (NER, BER, and HR) contributes to the cytotoxicity observed in BRCA1-deficient cells in the presence or absence of cisplatin. Thus COH29 could be exploited as a potent DNA repair inhibitor.

All cell lines were acquired from the American Type Culture Collection (Manassas, Va., USA). Cells were maintained in RPMI 1640 medium (Mediatech) with 10% fetal bovine serum, 2 mM glutamine, and 100 U of penicillin and 100 µg of streptomycin per ml of medium (Sigma) at 37° C. in 5% $CO_2$. To isolate HCC1437+BRCA1 cells, parental HCC1937 cells were transfected with pcDNA3.1 plasmid expressing full-length BRCA1 cDNA. Stable transfectant clones were selected and used for drug sensitivity assays. For stable transfection, cells at 30-40% confluence were incubated overnight with 2 mg of plasmid DNA, using FUGENE® 6 transfectin reagent (Roche Molecular Biochemical, Monza, Italy) according to the manufacturer's instructions. Cells were then selected in puromycin (1 µg/ml) (Invitrogen life Technologies, La Jolla, Calif., USA.) After 20 to 30 days, viable puromycin-resistant colonies from HCC1937 transfections were expanded and screened. The clones that stably expressed puromycin and retained growth potential were assayed for BRCA1 expression by Western blot analysis. By Western blot analysis, we evaluated the restoration of BRCA1 expression in the puromycin-resistant cDNA/transfectant cells. These transacted cells showed an increased expression of BRCA1 protein, suggesting effective restoration of protein expression.

COH29 was synthesized and purified at City of Hope. γ-H2AX was purchased from cell signaling (Danvers, Mass., USA). Rad51 was purchased from Novus (Littleton, Colo., USA). Beta-actin was from Millipore (Billerica, Mass., USA). Antibodies specific to FOXO3 (H-144 and N-16, 1:1000), phospho-H2AX serine-139 (γ-H2AX, 1:1,000), phospho-p53 serine-15 (p53-pS15, 1:1.000), Rad51 (1:1000), β-tubulin (1:1000), Lamin A/C (1:2000 dilution) PARP, and anti-mouse, and anti-rabbit IgGs were obtained from Santa Cruz Biotechnology (Santa Cruz, Calif., USA). Abs against FOXO3 (1:1000) and phospho-ATM serine-1981 (ATM-pS1981, 1:1,000 dilution) were obtained from Epitomics (Burlingame, Calif.) and Millipore (Billerica, Mass.), respectively. An Ab against p53-pS15 was purchased from Cell Signaling Technology (Danvers, Mass.). An anti-p27Kip1 Ab was purchased from BD PharMingen (San Diego, Calif.). Alexa 488 (green)- and Alexa 594 (red)-conjugated secondary Abs were obtained from Molecular Probes (Eugene, Oreg.). Anil-Rabbit IgG (whole molecule)-FITC antibody was purchased from Sigma (St. Louis, Mo., USA). RHODAMINE RED-X™ Goat Anti-Mouse IgG was purchased from Invitrogen (Carlsbad, Calif., USA).

Immunofluorescence experiments were conducted as described previously (21,22). Specifically, A549 cells were grown on glass coverslips. After treatment with COH29 (1 or 10 μM) for 24 or 48 hours, cells were fixed with 4% paraformaldehyde for 10 min and permeabilizsd with TRITON™ X-100 (0.5%). The coverslips were washed with phosphate-buffered saline (PBS) and blocked with PBS-containing 2% bovine serum albumin (BSA), incubated with an Ab specific to FOXO3 or ATM-pS1981 or γ-H2AX or p53-pS15 (1:50-1:200 dilution), followed by Alexa 488-conjugated anti-rabbit or anti-mouse (1:200). Alexa 594-conjugated anti-goat (1:100) secondary Abs (Molecular Probes). Cells were incubated with 4',6-diamidino-2-phenylindole (DAPI; Sigma) to stain the nuclei. Specific staining was visualized and images were captured with a Leica SF2 AOBS confocal laser scanning microscope. To measure foci-positive cells, we used ~300 cells randomly captured by confocal microscopy. The percentages of considering foci-positive cells were calculated from cells containing at least five foci. Each error bar presented is the mean of standard deviation.

For subcellular fractionation, cells were trypsinized and washed with cold PBS solution twice. After centrifugation at 1,200 g for 5 min, cells were incubated in buffer (50 mM HEPES, pH 7.5, 150 mM NaCl, 1 mM EDTA) containing 0.2% NONIDET™ P-40 (NP-40), supplemented with protease inhibitors (5 μg/ml each of pepstatin, leupeptin, and aprotinin) and phosphatase inhibitors on ice for 5 min. Following centrifugation at 1,000 g for 5 min, the supernatant was collected (i.e., cytoplasmic fraction) and pellets were washed with the same buffer twice. The washed samples were extracted for 40 min on ice with fractionation buffer containing 0.5% NP-40 for nuclear fraction. All the samples were sonicated and clarified by centrifugation at 16,000 g for 15 min. Protein concentrations of all fractions were determined with Bio-Rad Protein Assay (Bio-Rad Laboratories, Hercules, Calif.). Immunoblotting was performed as described previously (21,22). Briefly, equal amounts of boiled protein samples were subjected to SDS-polyacrylamide gel electrophoresis (PAGE) and transferred onto nitrocellulose membranes (Bio-Rad Laboratories). Membranes were blocked for 1 hour in 3% BSA in Tris buffered saline containing 0.05% Tween 20 (TBST) and incubated for 1 hour with primary antibody (1:500 or 1:1000) diluted in TBST containing 1% BSA. After two washes with TBST, membranes were incubated for 1 hour with horseradish peroxidase-conjugated secondary Abs (1:3000 dilution) at room temperature. The immunoblots were visualized on film with the West-Q chemi-luminescence kit (GenDEPOT, Barker, Tex.).

The MTT cytotoxicity assay was performed by incubating with MTT and monitoring the MTT formazan formed by viable cells with a microplate reader at a wavelength of 560 nm; the survival, ratio was determined using the formula:

$$(A_{test} - A_{blank})/(A_{control} - A_{blank}) \times 100\%.$$

The cytotoxicity was determined in 96-well plates using the semiautomatic fluorescence-based Digital Imaging Microscopy System (DIMSCAN). DIMSCAN uses digital imaging microscopy to quantify viable cells, which selectively accumulate FDA (fluorescein diacetate; Alfa Aesar, Ward Hill, Mass.). DIMSCAN is capable of measuring cytotoxicity over a 4 log dynamic range by quantifying total fluorescence per well (which is proportional to the number of viable cells) after elimination of the background fluorescence by digital thresholding and eosin Y (Mallinckrodt Baker, Center Valley, Pa.) quenching. Cells were seeded into 96-well plates in 100 μL of complete medium at 2,000 to 5,000 cells per well depending on cell line growth rate. After overnight incubation, test compound was added to each well at various concentrations in 50 μL of culture medium. After incubation with the drugs for 96 hours at 37° C., FDA (final concentration: 10 mg/mL) and eosin Y [final concentration: 0.1% (w/v)] were added to each well and the cells were incubated for an additional 20 minutes at 37° C. Total fluorescence per well was then measured using DIMSCAN, and the results were expressed as the ratio of the fluorescence in treated wells to the fluorescence in untreated wells (survival fraction).

Orthotopic Tumor Model.

Experiments in mice were conducted under a protocol approved by the IACUC of City of Hope. Because HCC1937 and HCC1937+BRCA1 cells from slow-growing tumors, they were implanted using MATRIGEL™ (Becton-Dickinson Biosciences). To establish tumors $4 \times 10^6$ cells in 200 μL serum-free medium containing 50% MATRIGEL™ were injected into the mammary fat pads around the inguinal area of a pair of 8 week old female NSG mice. Once the initial tenors reached 13 mm in diameter, they were dissected out minced into 3 mm pieces and implanted into the inguinal area of the mammary fat pads of the experimental mice Tumors were measured over a 28-day period, and for each time point, the student t-test was used to determine the statistical significance between daily gavage with 400 mg/kg COH29 in 30% solutol and corresponding vehicle control. The p value less than 0.05 (2 sides) was considered to indicate statistical significance The EJ2 cells were generated to evaluate Alt-NHEJ through monitoring the fluorescence intensity of GFP and EJ5 cells were used to determine NJEJ as described previously. (23) Cells were seeded into 6-well plate and treated with COH29 or cisplatin at different concentration for 24 hours. The cells were then trypsinized, washed, and analyzed by flow cytometry.

The construction of the anti-human BRCA1 siRNA-expressing plasmid was perforated as previously described (24). Thus, previously published anti-human BRCA1 siRNA sequences were utilized (5'-UCACAGUGUC-CUUUAUGUA-3" [SEQ ID NO: 1] and 5'-UA-CAUAAAGGACACUGUGA-3' [SEQ ID NO:2]). In each case, the annealed oligonucleotide duplex encoding the siRNA was subcloned into the expression vector psiRNA-hH1zeo (InvivoGen, San Diego, Calif., USA) to express under the control of the RNA polymerase III-dependent H1

RNA promoter. Cells were transfected with the indicated plasmid at equimolar concentration via electroporation.

Total RNA was isolated using RNEASY® Micro Kit (Qiagen Inc.). Genomic DNA contamination was removed with DNAse I treatment. The integrity of isolated RNA was examined via electrophoresis through 1% agarose gel (SeaKem, FMC, Rockland, Me., USA) or with an Agilent 2100 Bioanalyzer (Agilent Technologies, Santa Clara Calif., USA). The RNA concentration ($A_{260}/A_{280}$ ratio) was determined by UV spectrophotometry. The cDNA was prepared from total RNA using MMLV reverse transcriptase and random hexamers as primers (Invitrogen). Gene, expression was quantified using cDNA samples through real-time PCR. Primers for BRCA1 were purchased from APPLIED BIOSYSTEMS®, Foster City, Calif., USA. Additional primers and probes for 18S and β-actin were designed according to the APPLIED BIOSYSTEMS® guidelines (PRIMER EXPRESS® software; APPLIED BIOSYSTEMS®) to fit the real-time PCR requirements. The sequences of primers are
AGGAATTGCGGGAGGAAAATGGGT (SEQ ID NO:3) and
GCCCCCTGAAGATCTTTCTGTCCT (SEQ ID NO:4).

The PARP1 activity was determined using the PARP1 Chemiluminscent Assay Kit (BPS Bioscience, San Diego) according to the manufacturer's protocol. Briefly, the ribosylation reaction was carried out with activated DNA in PARP assay buffer using test inhibitor, positive control, substrate control and blank reactions, for 1 hour at 25° C. Detection was by streptavidin-HRP with chemiluminescent substrate A and B read in a luminometer.

Zebrafish (*Danio rerio*) were obtained from zebrafish Core facility of Taipei Medical University and maintained at 28° C. on a 14 h light/10 h dark cycle. Embryos were incubated at 28° C. and different developmental stages were determined as described (25). Wild-type embryos were treated with different concentrations of HU (0, 5, 30, 20, 50 mM) or COH29 (0, 10, 20, 50, 100 μM) at 20 hpf to evaluate the mutagenic effect. Fifteen embryos were treated per well condition. Treated embryos were observed at 2, 3, 4, 5 and 6 dpf. At 6 dpf, the percentage of fish exhibiting developmental abnormalities and the survival rate was determined. Embryos were observed using an Olympus IX70-FLA inverted fluorescence microscope. Images were taken using SPOT digital camera system (Diagnostic Instruments, Sterling Heights, Mich., USA) and assembled with ImageJ software (26).

Microarray samples were RMA normalized (27) using PARTEK® GENOMICS SUITE™ (Version 6.6; Partek, Inc.), and genes were defined as differentially expressed if they showed at least a 1.2 fold-change and false discovery rate (FDR)<0.05. FDR values were calculated using the method of Benjamini and Hochberg (28) from the distribution of ANOVA with Linear Contrast p-values. Gene ontology (GO) (29) enrichment analysis was performed within PARTEK® GENOMICS SUITE™, and GO categories were defined significant with a Fisher Exact test p-value<0.05.

RRM2-PARP1 correlation analysis was determined from gene expression profiling of 289 paraffin embedded breast cancer tumor samples using AFFYMETRIX® U133 A&B (GSE4922) based on the Ivshina et al. study. (30) Statistical analysis was performed using Bioconductor R package, 64 bit, v 3.0.2. (31) Correlation analysis was conducted using Spearman's rank correlation. A level of $P<0.05$ and $r>0.5$ was considered statistically significant.

The in vitro replication of the pSYO+ plasmid containing the SV40 replication origin was carried out as previously published (26) with modifications. The final 25 μL reaction volume contained 30 mM HEPES (pH=7.2), 7 mM $MgCl_2$, 0.5 mM DTT, 5 μCi [α-$^{33}$P]-dCTP, 1 μM dCTP, 100 μM each of dTTP, dCTP, and dGTP, 200 μM each of CTP, UTP, and GTP, 4 mM ATP, 40 mM of phosphocreatine, 50 μg of creatine phosphokinase, 50 ng of pSVO+, 0.1-1.0 μg T Ag (optimal concentration determined by titration assays), and optimal amount of HeLa extract (determined by titration assays) (Chimerx; Milwaukee, Wis.). To quantify DNA replication inhibition, HeLa extract was incubated with increasing concentrations of COH29 for 30 minutes prior to the start of the reaction. The HeLa-compound mixture was added to the remaining SV40 DNA replication components, incubated at 37° C. for 1 hour, spotted on WHATMAN® DE81 filters, washed with 100 mM sodium pyrophosphate (pH 7.4) and 300 mM ammonium formate (pH 7.4), then dried. The amount of radiolabeled material incorporated into newly synthesized daughter DNA strands was then determined by liquid scintillation counting.

Without being bound by any particular theory, COH29 anticancer activity may stem at least in part from the inhibition of human ribonucleotide reductase (hRR), which is an enzyme for the biosynthesis of deoxyribonucleotides for DNA replication. In addition, as a component of the base excision repair complex, ribonucleotide reductase is also involved in DNA repair. Consequently, in embodiments, COH29 was discovered herein to target several additional components of the repair complex. Furthermore, in embodiments, BRCA1-defective human breast or ovarian cancer cells are more sensitive than wild-type BRCA1 counterparts to COH29. In embodiments, COH29 exhibits synergy with the DNA crosslinking drugs, such as cisplatin, in BRCA1 mutant cells. In embodiments, COH29 was discovered herein to suppress RAD51, which, without being bound by any particular theory, is involved in the repair of double strand breaks (DSB) by the homologous recombination (HR) pathway. In embodiments, COH29 targets multiple DNA repair pathways and potentially modulates backup DNA repair resulting from the genetic background (mutation). In embodiments, COH29 may overcome acquired resistance to PARP inhibitors (e.g. PARP1 inhibitors). Pharmacologically, and without being bound by any particular theory, COH29 was discovered herein to suppress gemcitabine-resistant human cancer cell proliferation and synergizes with cisplatin or γ-irradiation.

COH29 is an aromatically substituted thiazole compound that, without being bound by any particular theory, occupies a structurally conserved ligand-binding pocket on the hRRM2 subunit located at the hRRM1/hRRM2 interface. In embodiments, binding to this pocket inhibits the hRRM1/hRRM2 assembly, effectively inhibiting RR activity. In vitro COH29 is active in multiple human cancer cell lines and was shown to be highly potent with an $IC_{50}$ less than 10 μM in most cases. COH29 has been shown to possess broad activity in the NCI-60 cell line panel, and that multiple human breast cancer cell lines including, for example, human ovarian cancer cell lines, are sensitive to COH29 (6). Breast and ovarian cancers occur with a greater frequency in carriers of a mutant BRCA1 gene than the general population (32). Accordingly, herein, it was investigated whether human cancer cells defective in BRCA1 demonstrated greater sensitivity to COH29. Indeed, as shown in FIG. 1A the UWB1.289 ovarian cancer cell line, which expresses truncated BRCA1 protein due to the homozygous 2594delC mutation (33), was more sensitive to COH29 ($IC_{50}$: 12.30±1.15 μM) than the OV90 human ovarian, cancer cell line that express wild-type BRCA1 ($IC_{50}$: 31.57±3.35 μM).

The effect of COH9 was assessed in breast cancer cells with an identical genetic background, which differed only in BRCA1 expression to determine the extent that mutant BRCA1 increased cytotoxicity. First, the effect of silencing BRCA1 expression was examined. HCC1937 are human breast cancer cells homozygous for an insertion mutation, resulting in the endogenous expression of a truncated BRCA1 protein (34) and HCC1937+BRCA1 is a stable transfectant clone expressing the human wild-type BRCA1 protein. BRCA1 expression was suppressed by RNA interference in these cells. After 72 h treatment, with 10 μM COH29 72% of HCC1937+BRCA1 cells transfected with control siRNA survived. In contrast only 53% of the cells transfected with BRCA1 siRNA survived. The effect of restoring wild-type BRCA1 expression on COH29 cytotoxicity was investigated by comparing HCC1937 and HCC1937+BRCA1 cells. When treated with varying doses of COH29 for 72 h, cells expressing wild type BRCA1 were much less sensitive to COH29 ($IC_{50}$: 35.01±3.63 μM) than the BRCA1 mutant HCC1937 cells ($IC_{50}$: 7.25±0.64 μM). Real-time reverse transcriptase polymerase chain reaction (RT-PCR) showed that HCC1937+BRCA1 cells express ~25 fold higher level of BRCA1 than HCC1937.

Figure 1B:
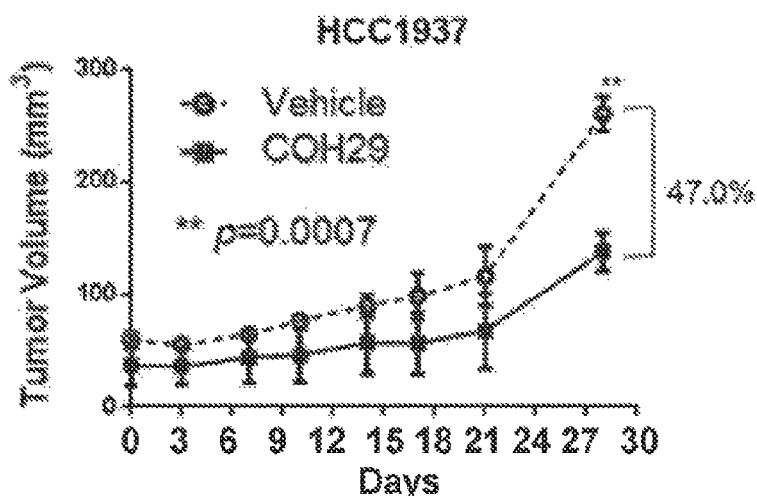
Figure 1C:
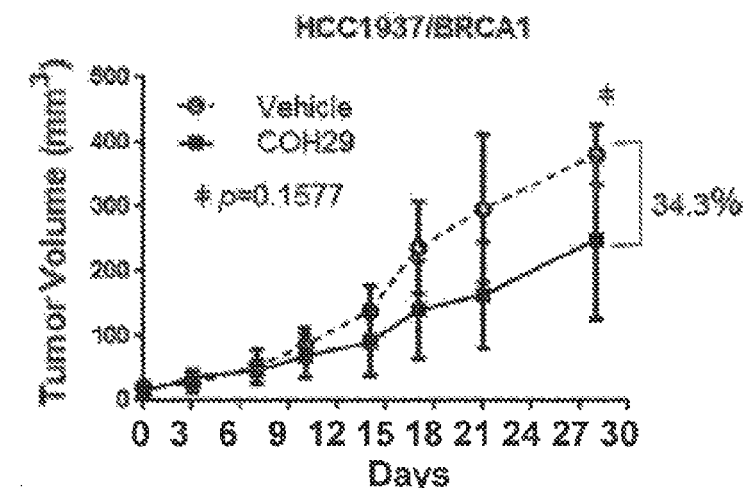
(FIG. 1C) cells in the mammary fat pads of female NSG mice (mice were treated with COH29 or vehicle as indicated—results are the mean±standard error of tumor measurements from 4 mice/group).

The sensitivity of BRCA1 deficient cells to COH29 was further confirmed in an orthotopic tumor explant model. The growth of HCC1937 tumors implanted into mouse mammary fat pads was significantly (p=0.0007) suppressed by daily oral dosing with 400 mg/kg COH29 compared to vehicle (FIG. 1B). In contrast, tumors established with the isogenic HCC1937+BRCA1 cells were not significantly smaller in COH29 treated mice than in vehicle controls (p=0.1577; FIG. 1C).

The impact of the BRCA1 mutation on response to COH29 treatment in ovarian cancer cells was also examined. UWB1.289+BRCA1 are a stable transfectant clone of ovarian cancer cells expressing the human wild-type BRCA1 gene, and UWB1.289 are parental cells that were transfected with a control plasmid expressing the neomycin-resistance gene. These cells were treated with varying doses of COH29 for 72 h. Cells expressing wt BRCA1 were less sensitive to COH29 ($IC_{50}$: 23.52±2.38 μM and 12.30±1.15 μM for UWB1.289+BRCA1 and UWB1.289, respectively), RT-PCR assay showed that UWB1.289+BRCA1 cells express ~3.08 fold higher level of BRCA1 than UWB1.289. These results suggest that COH29 may induce greater lethality in human cancer cells detective in BRCA1. Additional pharmacological data for COH29 are provided as Tables 1 and 2. Of particular significance is the finding that COH29 suppresses the growth of various human cancer cells resistant to gemcitabine or cisplatin (Table 1).

TABLE 1

Comparison of the Effect of COH29 and Various Antineoplastic Treatments

| Comparison | Cell line | Antineoplastic Treatment $IC_{50}$ mean ± SEM | | | | |
| --- | --- | --- | --- | --- | --- | --- |
| | | COH29 (μM) | Gemcitabine (nM) | Cisplatin (μM) | Paclitaxel (nM) | γ-ray (Gy) |
| Human ovarian cancer cell lines | OV90 | 31.57 ± 3.35 | 78.27 ± 11.63 | 1.57 ± 0.29 | 9.09 ± 0.41 | >6 |
| | TOV112D | 16.00 ± 2.08 | 28.35 ± 4.18 | 1.32 ± 0.20 | 6.45 ± 1.05 | 5.30 ± 0.98 |
| | OVCAR-3 | 20.50 ± 0.81 | 118 ± 18.5 | 1.64 ± 0.04 | 2.89 ± 0.07 | — |
| | OVCAR-4 | 11.25 ± 1.51 | 55.15 ± 3.55 | 2.25 ± 0.25 | 5.55 ± 0.05 | — |
| BRCA1-defective vs WT in ovarian cancer | UWB1.289 | 12.30 ± 1.15 | 56.48 ± 0.32 | 1.43 ± 0.87 | 13.88 ± 0.70 | — |
| | UWB1.289 + BRCA1 | 23.52 ± 2.38 | 42.22 ± 0.62 | 7.40 ± 2.02 | 12.96 ± 1.62 | — |
| Gemcitabine-resistant vs cisplatin-resistant | KB-Gem | 7.5 ± 0.29 | 60.00 ± 10.00 | 0.38 ± 0.03 | 1.95 ± 0.15 | — |
| | KB-7D | 8.48 ± 0.27 | 0.69 ± 0.02 | 7.50 ± 0.30 | 5.17 ± 0.17 | — |
| Cisplatin-sensitive vs resistant ovarian cells | A2780 | 4.67 ± 1.64 | 25.51 ± 1.66 | 0.69 ± 2.11 | 3.60 ± 1.67 | — |
| | A2780-DDDP | 6.47 ± 1.41 | 36.30 ± 0.79 | 5.02 ± 1.18 | 11.38 ± 1.49 | — |
| TNBC | MDA-MB-231 | 9.70 ± 1.52 | 17.00 ± 1.33 | 3.74 ± 0.21 | 2.01 ± 0.57 | 3.60 ± 1.22 |

To identify the mechanism through which COH29 preferentially lyses BRCA1-mutant human cancer cells, we performed genome-wide microarray analysis using the AFFYMETRIX® GENECHIP® microarray platform to identify the gene expression profiles and pathways affected by COH29 treatment. The RNA expression profile of COH29 treated HCC1937 breast cancer cells lacking BRCA1 was compared wish that of COH29 treated HCC1937+BRCA1 cells. Both HCC1937-COH29 and HCC1937+BRCA1-COH29 cells showed Gene Ontology (GO) enrichment for DNA repair genes (Table 1a; p-values ranging from 0.046-0.0069), suggesting that COH29 interferes with DNA repair pathways. For example, DNA ligation involved in DNA repair is more strongly enriched in HCC1937 cells which may relate to the phenotypic effect. In BRCA1 wild-type cells, COH29 induced DNA damage signaling and suppressed BRCA1 and Rad51 expression, suggesting COH29 may inhibit the homologous recombination (HR) pathway to maintain double strand breaks (DSB) induced by COH29-activated DDR (DNA-damage response).

TABLE 1a

Gene Ontology Enrichment of Genes Downregulated by COH29 Treatment

| | HCC1937-COH29 vs HCC1937 | | HCC1937 + BRCA1-COH29 vs HCC1937 + BRCA1 | |
| --- | --- | --- | --- | --- |
| | P-value: | Genes (n) | P-value: | Genes (n) |
| DNA repair | 0.018 | 17 | $1.6 \times 10^{-5}$ | 44 |
| DNA ligation involved in DNA repair | 0.00065 | 3 | 0.0066 | 3 |
| DSB repair | 0.0015 | 7 | $6.9 \times 10^{-5}$ | 14 |
| DSB repair via HR | 0.0069 | 5 | 0.0046 | 9 |
| DSB repair via NHEJ | 0.049 | 2 | 0.041 | 3 |

Figure 2A:
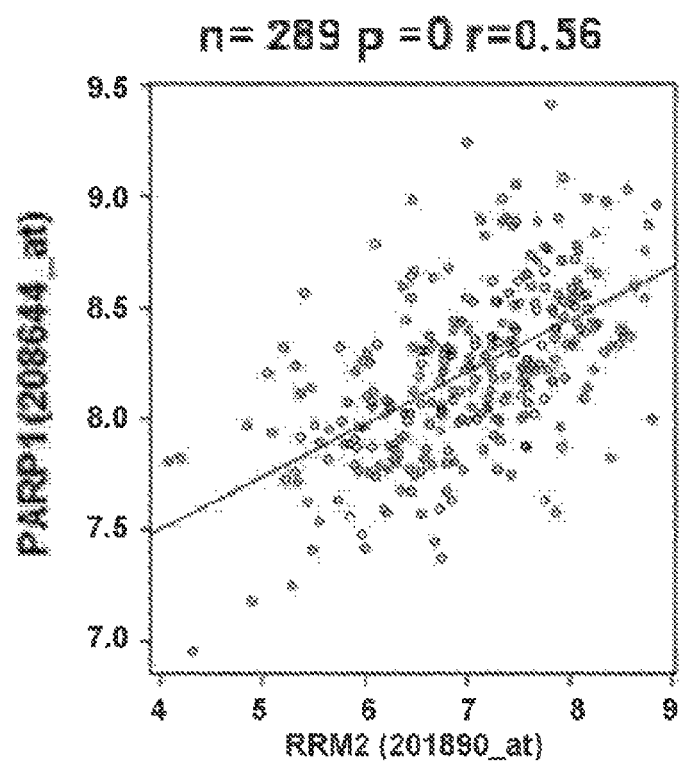
FIGS. 2A-2B. Correlation of RRM2 expression with PARP1 in patient cohorts. Regression plots of the expression of RRM2 and PARP1 extracted from public databases of clinical outcomes in (FIG. 2A) breast cancer and (FIG. 2B) ovarian cancer.
Figure 2B:
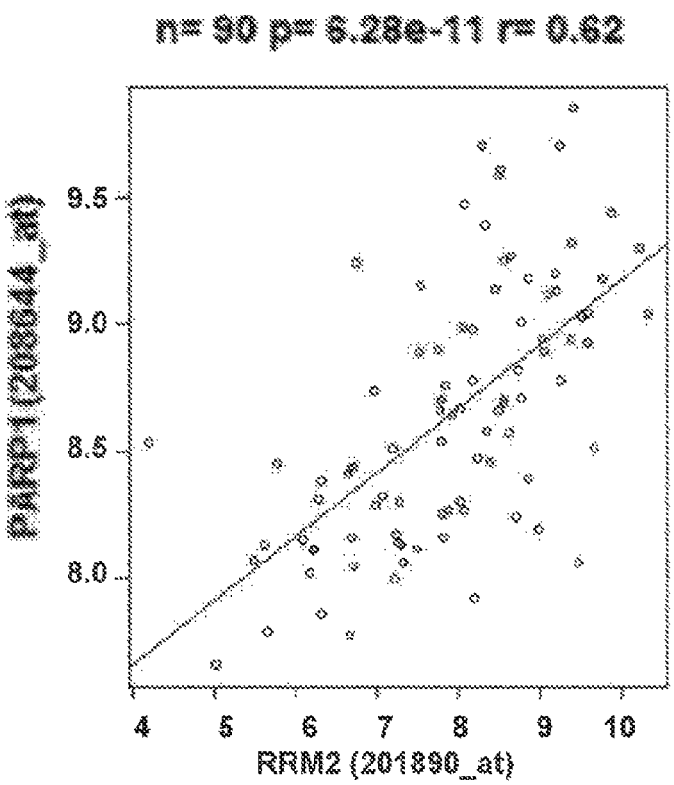

We additionally examined the publicly available gene expression studies in breast and ovarian cancer patient cohorts to verify gene expression correlations between RRM2 and PARP1. We found that there is strong correlation between RRM2 and PARP1 in Ivshina et al (30) study of breast cancer cohorts (n=289, P=0, r=0.56; FIG. 2A), as well as RRM2 and PARP1 gene expression correlation analysis in the study from Anglesio et al. (35) of ovarian cancer cohorts (n=90, p=0, r=0.62; FIG. 2B). Future genotype-phenotype correlation in selected patient cohorts may help to determine risk profiles for targeted treatments with COH29 in combination with traditional breast and ovarian chemotherapy.

To explore the mechanism through which COH29 preferentially lyses BRCA1-mutant human cancer cells, we sought to identify the target protein. We theorized, without being bound by any particular theory, that the expression profile of the target protein(s) may be affected through the interaction with COH29. For instance, the binding of COH-29 to a target protein may induce its degradation through, proteasome recruitment. The change in protein level may, in turn, alter the expression pattern of the corresponding gene. Microarray analysis was performed to identify the genes that are differentially expressed as a result of COH29 treatment. The RNA expression profile of COH29 treated HCC1937 breast cancer cells lacking BRCA1 was compared with that of COH29 treated HCC1937+BRCA1 cells. The clustering of differentially expressed genes is shown in FIGS. 2A-2B.

To determine if COH29 inhibited hPARP1, PARP1 activity was examined in lysates of cells treated with or without COH29 for 4 h, 8 h or 24 h. In human breast cancer HCC1937 cells lacking BRCA1 24 h COH29 incubation decreased PARP1 activity by 41.08% (726177 cps for untreated versus 427851 cps for COH29 treated), whereas it decreased by 12.66% (2336878 cps for untreated versus 2041097 cps for COH-29 treated) in similarly treated HCC1937+BRCA1 cells containing BRCA1 (FIG. 3A)

Figure 3A:
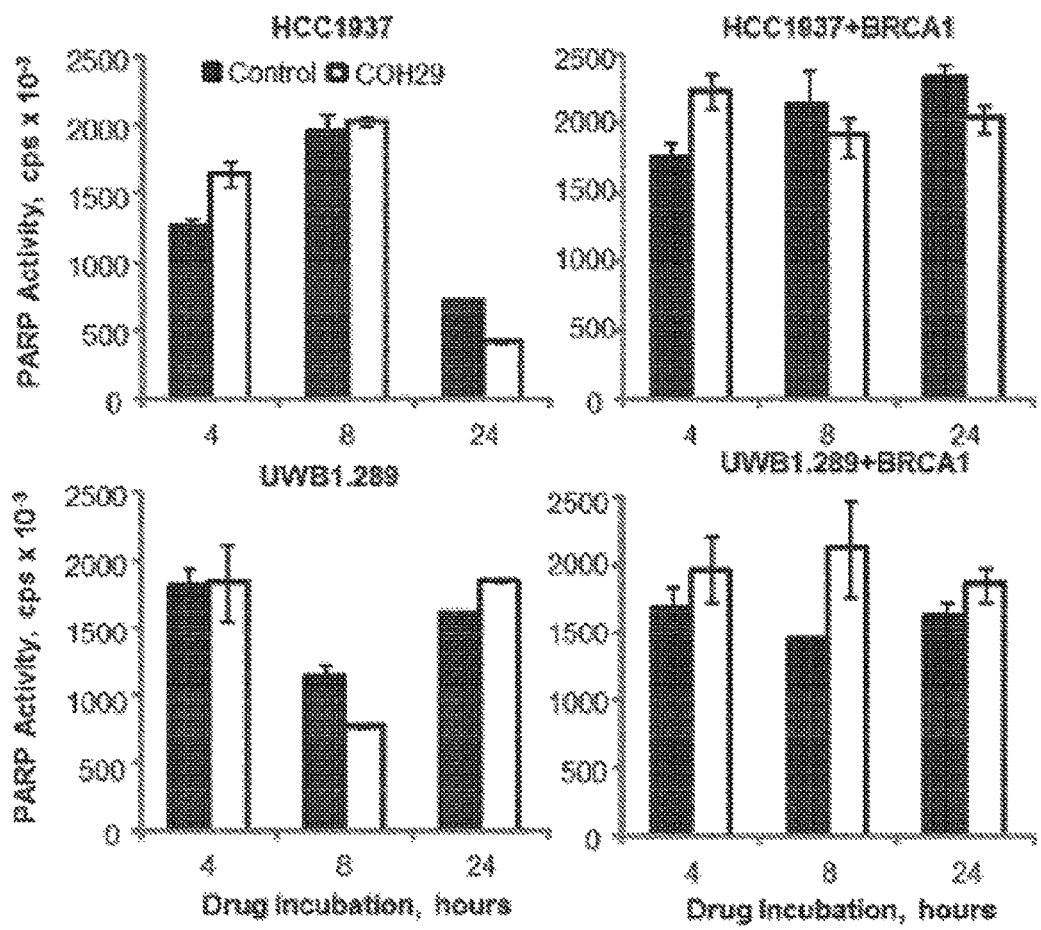
FIGS. 3A-3B. COH29 inhibits PARP1 in BRCA1-defective human breast cancer cells.

Inhibition of PARP1 by COH29 was more dramatic in the UWB1.289 human ovarian cancer line (FIG. 3A). PARP1 activity decreased by 31.79% (113559 cps for untreated versus 774611 for COH29 treated) in UWB1.289 cells lacking BRCA1 after 8 h COH29 treatment whereas it rose by 46.31% (145769 cps for untreated versus 2129944 cps for COH29 treated) in similarly treated UWB1.289+BRCA1 cells expressing wt BRCA1. Taken together, this indicates that COH29 inhibits PARP1 with greater efficacy in BRCA1-defective human cancer cells.

Figure 3B:
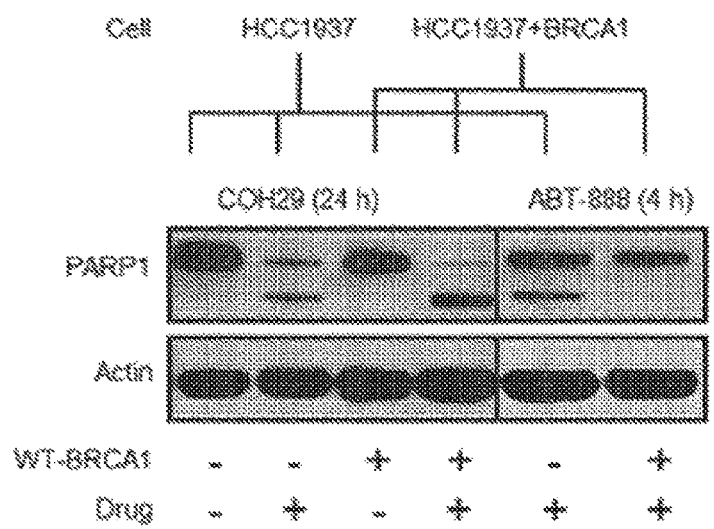

The effect of COH29 on PARP1 protein levels was also examined. Treatment with COH29 for 24 h attenuated PARP1 protein in HCC1937 BRCA1-defective breast cancer cells and to a lesser extent in HCC1937-BRCA1 wt cells (FIG. 3B). Little reduction was observed for 4 h COH29 treatment. In contrast ABT-888 treatment for 4 h led to a significant reduction of PARP1 in HCC1937 cells irrespective of their BRCA1 status (FIG. 3B).

Figure 4A:
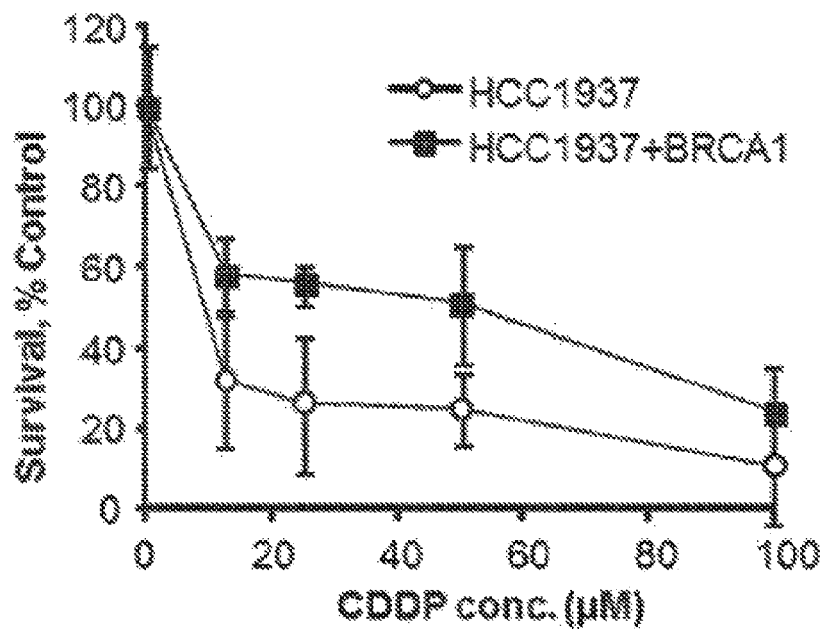
FIGS. 4A-4B. The effect of BRCA1 on cell survivability following the dual treatment with COH29 and cisplatin.
Figure 4B:
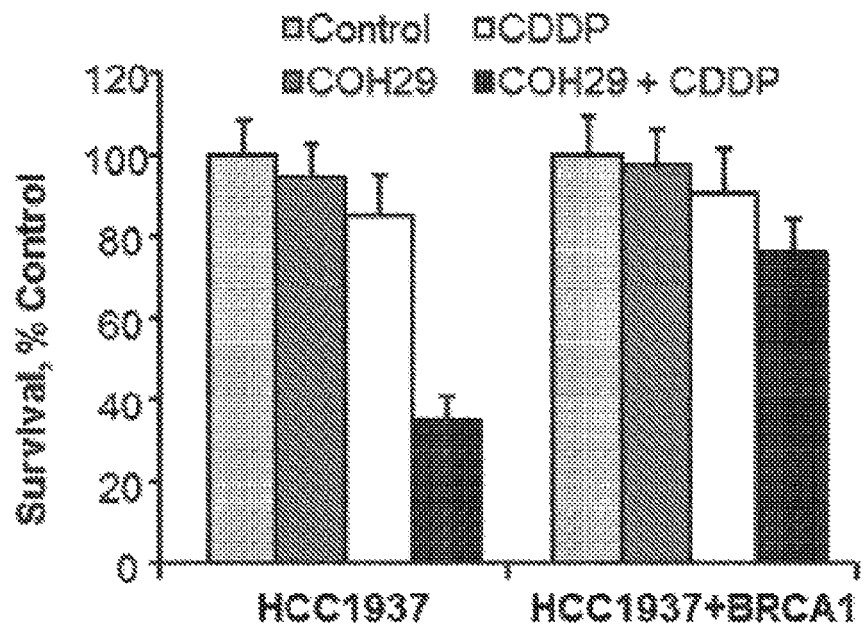

Synthetic lethality achieved through inhibiting PARP1 in a BRCA1-mutant cell background may augment cytotoxicity for DNA-damaging drugs. (18) Here, we investigated whether inhibition of PARP1 by COH29 enhances the cytotoxicity of cisplatin in BRCA1-defective human cancer cells. Cisplatin is a widely used chemotherapeutic whose anticancer activity is mainly attributed to DNA crosslinking in target cells. Stable transfectants of human breast cancer line HCC1937 expressing wt BRCA1 (HCC1937+) or control transfectant (HCC1937) cells were simultaneously treated with COH29 and cisplatin for 24 h. A significant reduction in survivability occurred in HCC1937 cells when compared to HCC1937+BRCA1 cells following treatment with the two drugs (FIG. 4A). Control experiments performed in parallel showed that a single treatment with either COH29 alone or cisplatin alone leads to a lesser yet similar level of impact for the two cell lines (FIG. 4B; also see Table 3). Additional synergy was observed between COH29 and gemcitabine or γ-irradiation (Table 2).

TABLE 2

Synergy of COH29 with Various Antineoplastic Treatments

| | Combination Score | | | | |
|---|---|---|---|---|---|
| Cell line | OV-90 | TOV112D | MDA-MB-231 | A2780 | A2780-CDDP |
| COH29 + Cisplatin | 1.45/Antagonistic | 1.2/0.81 | 3.07/0.93 | 1.09 | 1.08 |
| COH29 + Gemcitabine | 1.56/Antagonistic | 1.4/1.05 | 1.11/0.87 | 1.06 | 0.96 |
| COH29 + Radiation | 1.59/Antagonistic | 1.89 | 1.12/0.91 | ND | ND |

ND; not done

Figure 6:
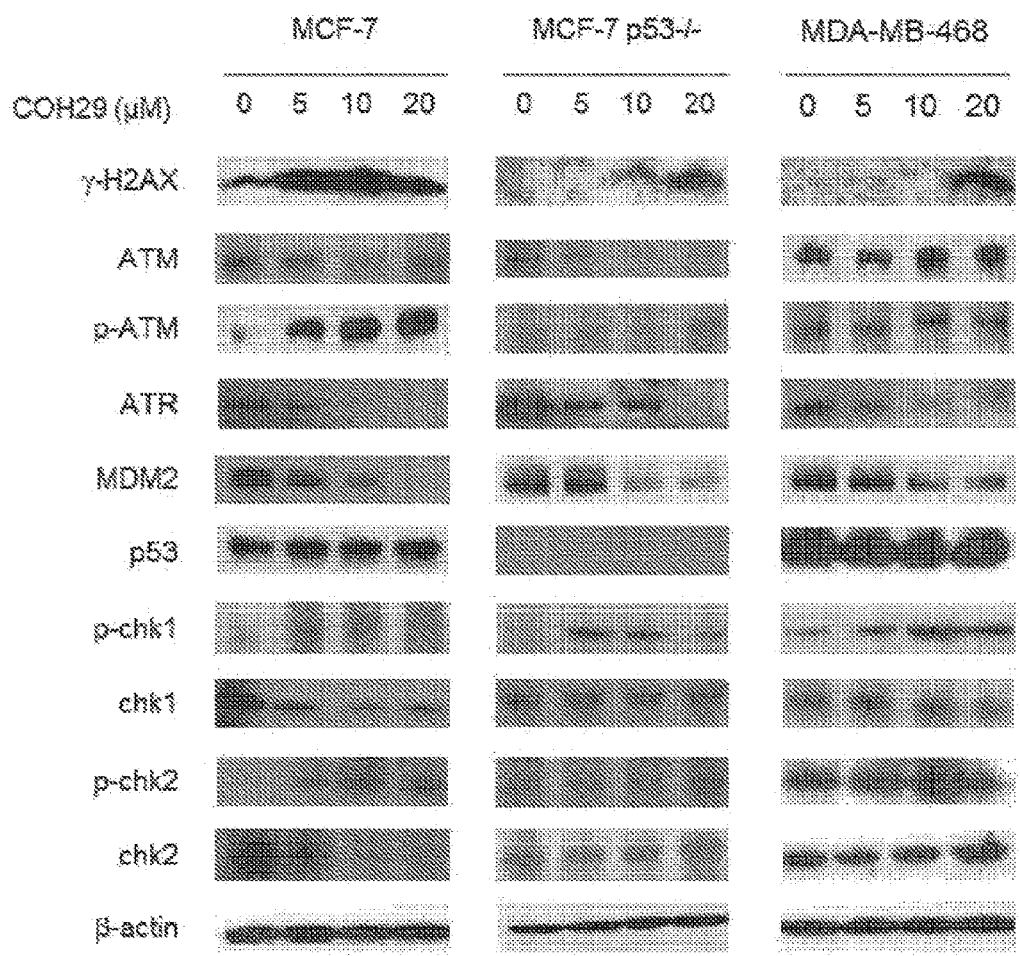
FIG. 6. COH29 treatment activates DNA damage checkpoint. The effect of COH29 treatment on DNA damage checkpoint, proteins in human breast cancer cells expressing wt p53 (MCF-7) or defective for p53 (MCF-7 p53−/−), and in triple-negative breast cancer cells (MDA-MB-468) assessed by Western Blot.

The RR-inhibiting drug hydroxyurea is known to be genotoxic (36,37). A similar consequence is expected for COH29 as it also inhibits RR. In human cells, such damage activates the DNA damage checkpoint to halt cell cycle progression to allow time for repair. Without being bound by any particular theory, the signaling initiated by the DNA damage is initially mediated by 'ataxia-telangiectsia-mutated' (ATM) and 'ATM and Rad 3-related' (ATR). Chk1 and Chk2 represent downstream, kinases for the signaling event, which phosphorylates Cdc25 phosphatase. Inhibition of Cdc25, in turn, suppresses the Cdk/cyclin complex, resulting in the cell cycle arrest (39). To assess the effect of COH29 treatment on the DNA damage checkpoint we employed two cell lines that differ in p53 status. COH29 treatment of MCF7 cells containing wild-type p53 activated the DNA damage checkpoint (FIG. 6 left panel) as evidenced by the phosphorylation of ATM. The downstream kinase CHK1 and CHK2 were also phosphorylated. In MCF7 cells lacking p53 (MCF-7 p53−/−), these proteins were also similarly modified following the COH29 treatment (FIG. 6 center panel). Following DNA damage, ATM or ATR phosphorylates γ-H2AX to recruit repair proteins to the site of damaged DNA (39). An increase in the γ-H2AX level occurred following the COH29 treatment in both cell lines. Thus, the COH29 treatment activates the DNA damage checkpoint in a p53-independent manner. Lastly, COH29's impact in 'triple negative' human breast cancer cells, which express a reduced level of progesterone receptor, estrogen receptor and Her2 receptor, was examined (33). When MDA-MB-468 cells were treated with COH29, a similar activation profile for the above kinases was observed (FIG. 6, right panel).

Figure 7A:
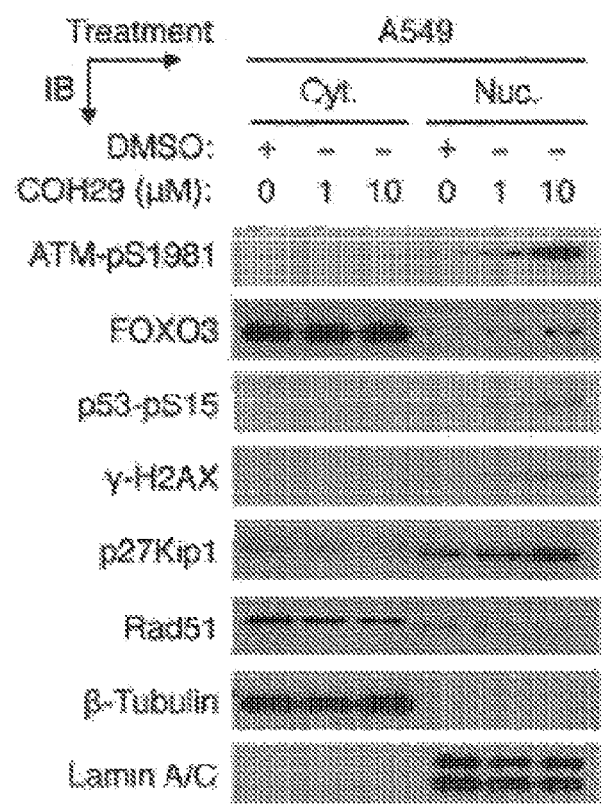
FIGS. 7A-7D, COH29 activates DDR and suppresses RAD51 expression in BRCA1 wild-type human lung cancer cells.
Figure 7B:
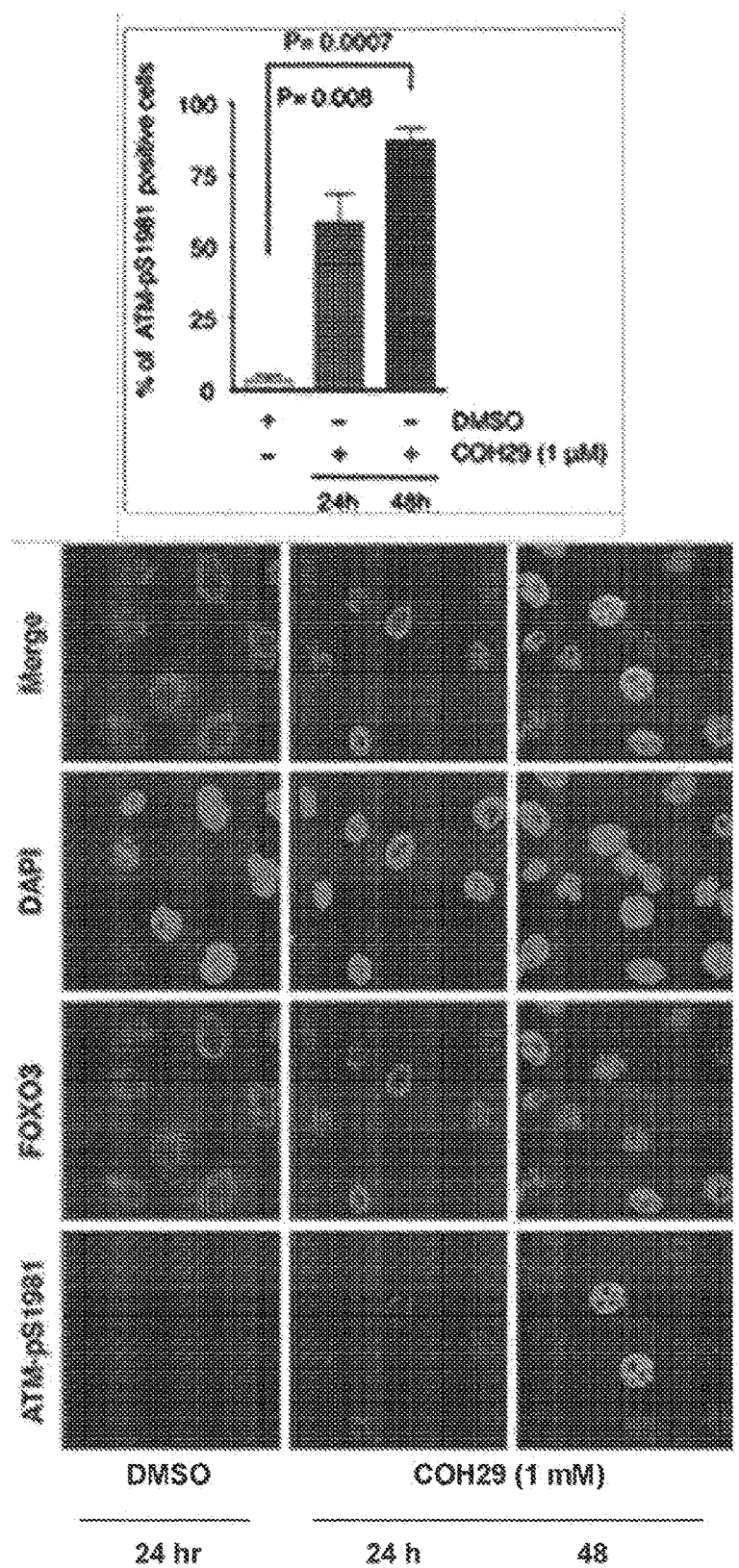
Figure 7C:
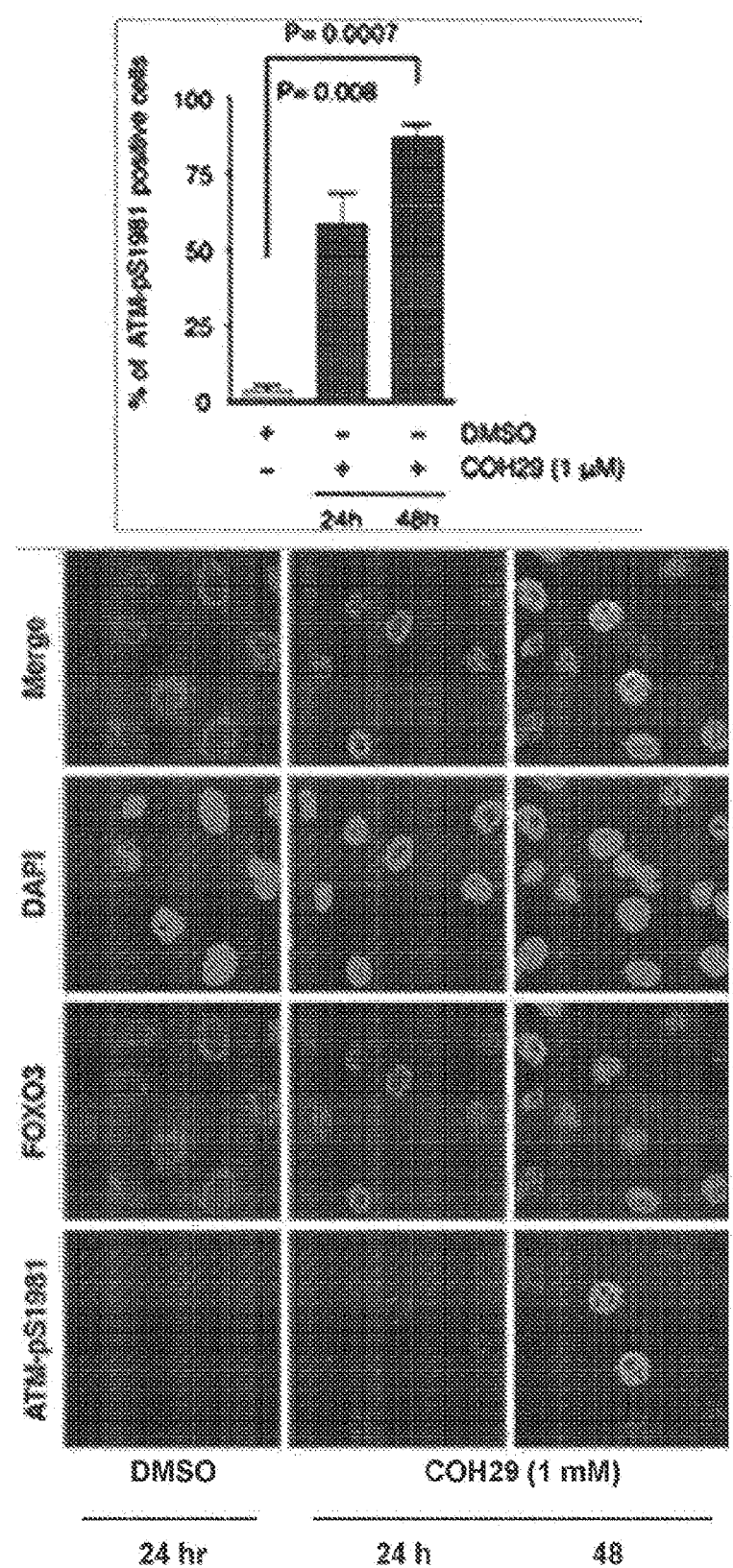
Figure 7D:
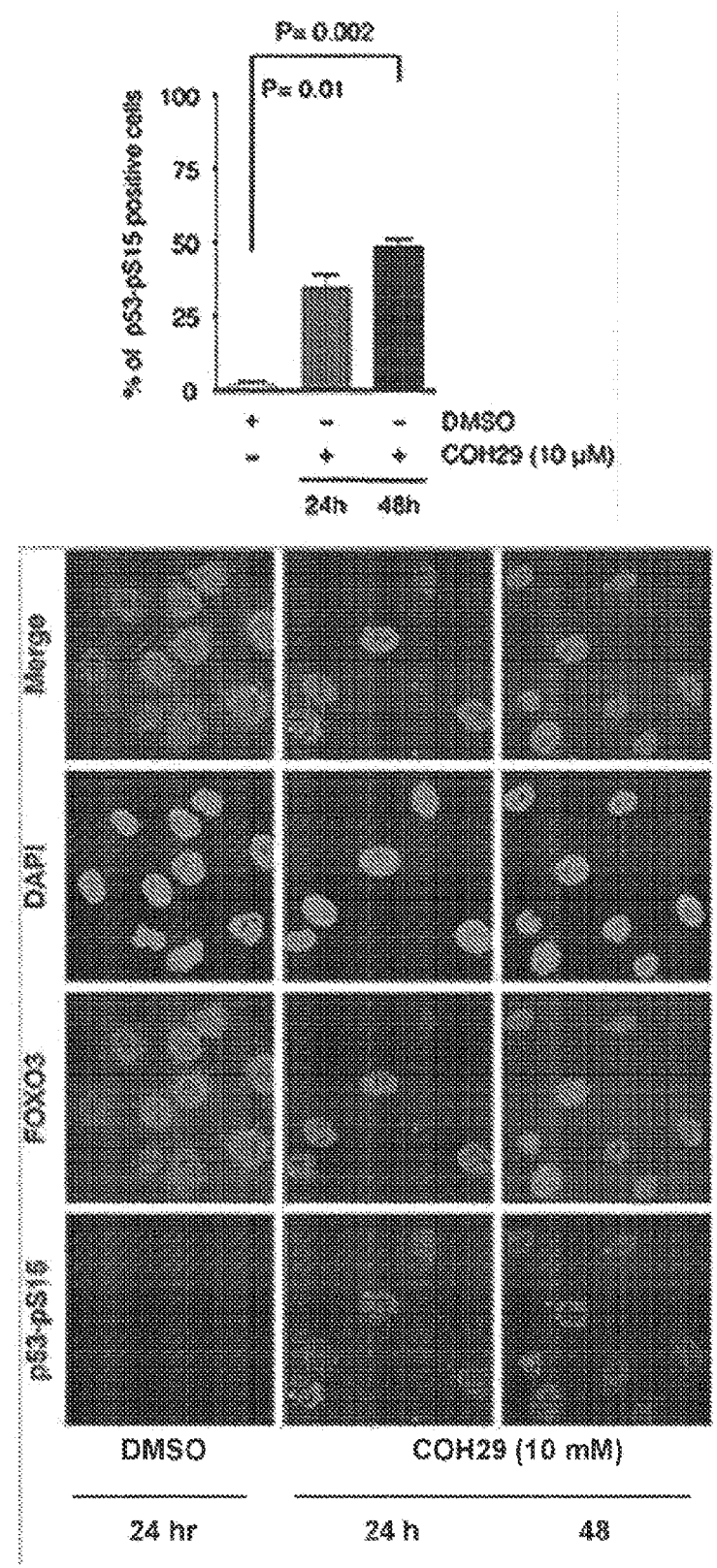
Figure 8A:
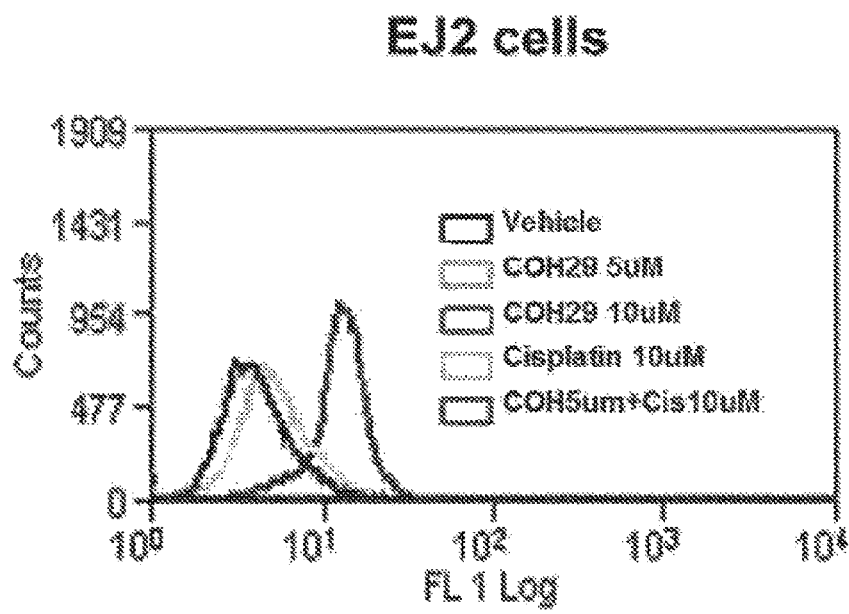
FIGS. 8A-8B. COH29 effect on NHEJ DNA repair. The activity of COH29 alone, or in combination with cisplatin at the doses shown, assessed by FACS analysis of EJ2 (FIG. 8A) (alternative NHEJ pathway) or EJ-5 (FIG. 8B) (NHEJ pathway) cells after 24 h exposure of the cells to the drugs.
Figure 8B:
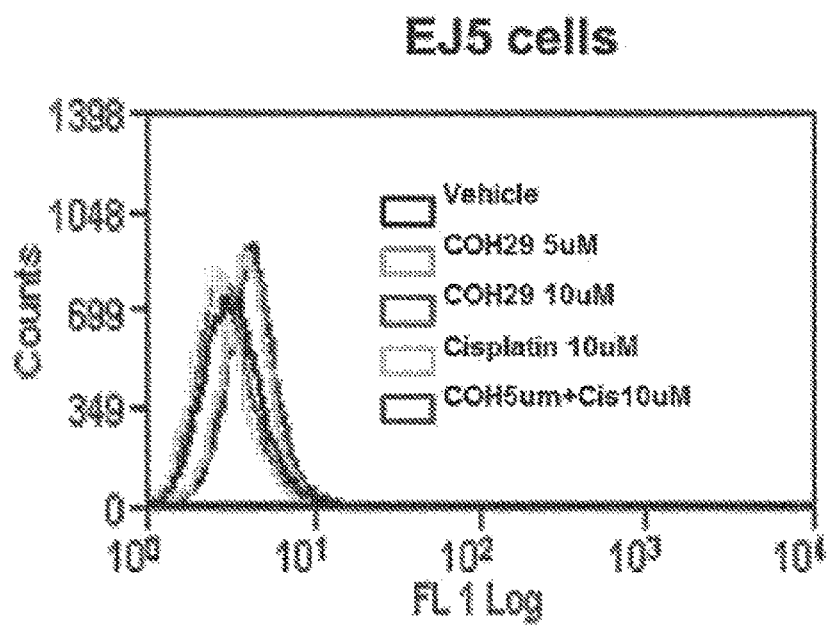
Figure 9A:
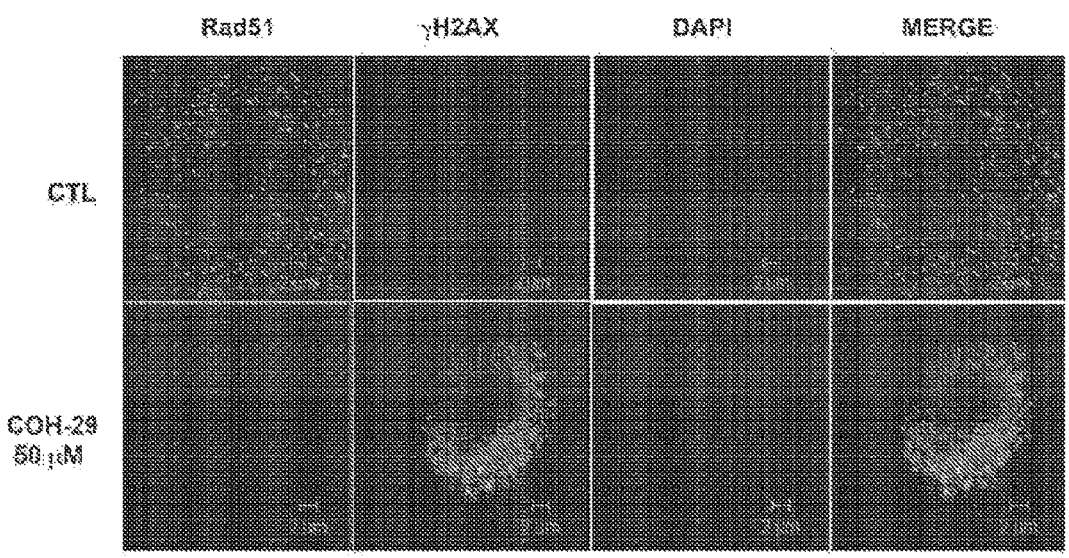
FIGS. 9A-9B. COH29 suppresses RAD51 in human lung cancer cells.
Figure 9B:
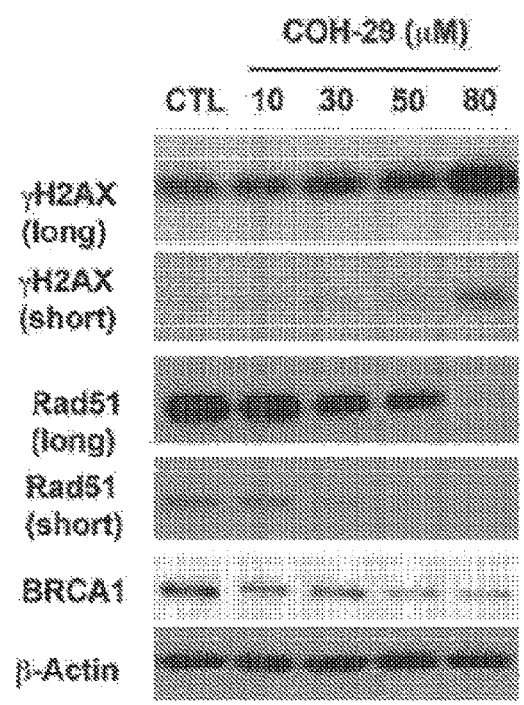

The effect of COH29 in BRCA1 wild-type cells was further evaluated. As shown in FIG. 7A, COH29 also induced accumulation of γ-H2AX, phospho-p53, and phospho-ATM in the nucleus. In addition, the induction of foxo3 and its target protein p27 in the nucleus was observed in COH29-treated cells (FIG. 7A). Moreover, we found that γ-H2AX phospho-p53, and phospho-ATM colocalize with foxo3 in the nucleus by confocal immunofluorescence microscopy (FIGS. 7B, 7C, and 7D). These results indicate COH29 induces DNA damage as well in BRCA1 wild-type NSCLC A549 cells. DNA double strand break (DSB) can be repaired either by homologous recombination (HR) or non-homologous end joining (NHEJ) pathway. To further elucidate the role of COH29 in DSB DNA repair, we determined COH29 had little effect on NHEJ repair efficient by the GFP-based chromosomal reporter EJ5-GFP in cells (FIGS. 8A-8B). However, the effect of COH29 on expression of crucial protein Rad51 responsible for HR repair was downregulated in the nucleus of BRCA1 wild-type NSCLC A549 cells by Western analysis (FIG. 7A). Furthermore, COH29 suppressed the protein level of BRCA1 and Rad51 foci formation, accompanied with accumulation of the DSB marker γ-H2AX in cells (FIGS. 9A and 9B), suggesting COH29 may be able to prolong DNA damage response (DDR)-induced DSBs by downregulation of the HR pathway in BRCA1 wild-type A549 cells.

Figure 5A:
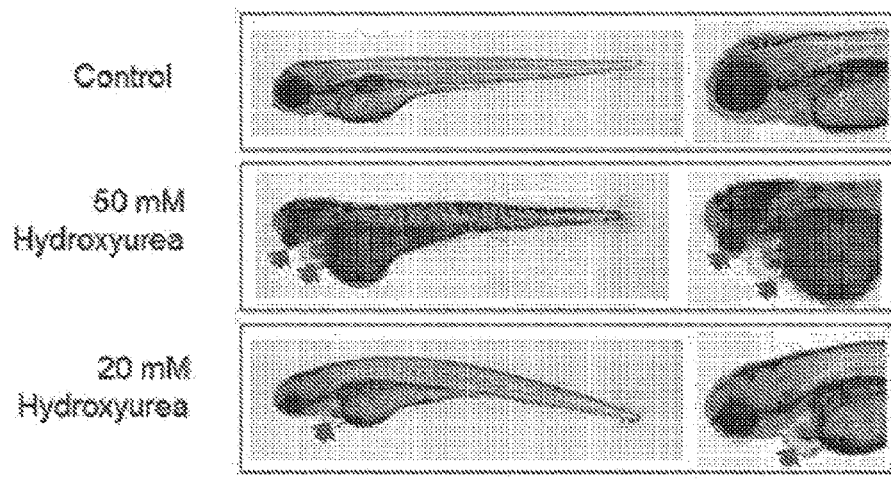
FIGS. 5A-5D. Effect of COH29 compared to HU in zebrafish genotoxicity assay.
Figure 5B:
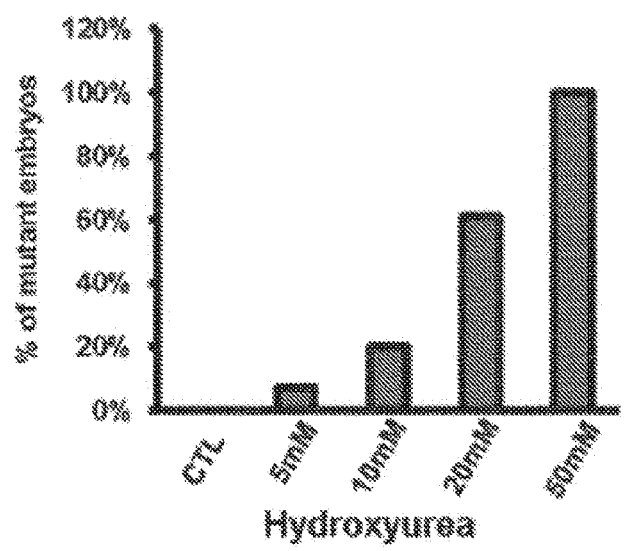
Figure 5C:
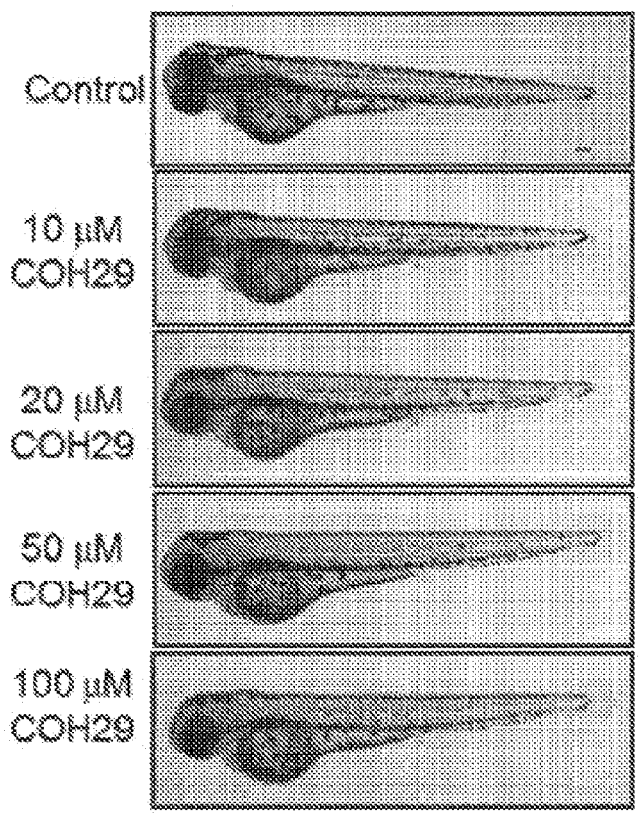
Figure 5D:
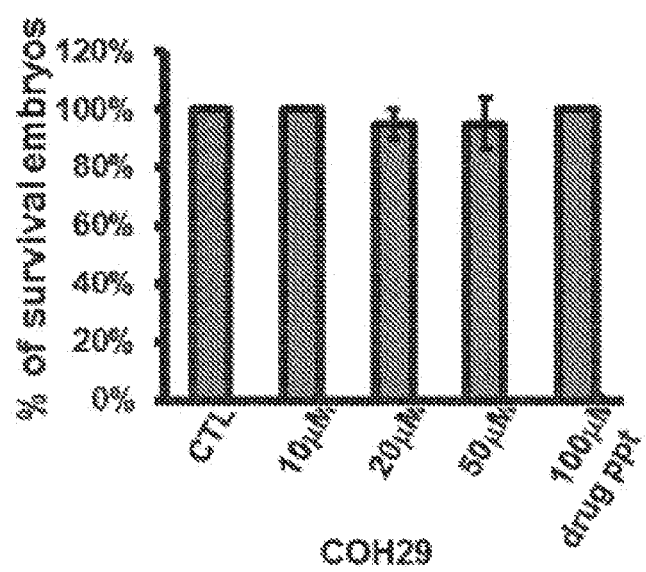

To assess the genotoxicity of COH29, wild-type zebrafish embryos were treated from 1 to 7 dpf (day post-fertilization) with a range of doses of COH29 (0-100 μM) and compared to embryos similarly treated with HU (0-50 mM) which is known to cause developmental defects. As expected, HU caused defects in eyes and heart by 4 dpf (FIG. 5A) and resulted in a dose-dependent increase in the number of mutant embryos (FIG. 5B). In contrast, no developmental defects (FIG. 5C) or decrease in viability (FIG. 5D) were observed in the presence of COH29.

Herein, COH29 was observed to be more active in BRCA1-deficient than in BRCA1 wild-type cell lines, in both in vitro and in vivo studies. BRCA1 is one of the mediators of cellular response to DNA damage. Accordingly, the differential gene expression analysis of COH29 treated BRCA1-deficient and BRCA1 wild-type cells performed herein, identified PARP1 as an additional inhibited protein. Furthermore, we discovered, inter alia, that COH29 augmented the activity of the DNA damaging agent, cisplatin. In addition, we discovered, inter alia, that COH29 activates the DNA damage checkpoint in p53 independent manner, and that nuclear Rad51 is downregulated.

In trying to integrate the above observations, we propose the following scenario. Without being bound by any particular theory, we propose that in human cells, damage to DNA such as the crosslinks formed by cisplatin is normally repaired through the BER pathway. As RR provides dNTPs necessary for the repair, the enzyme is closely involved in BER that occurs during S phase. In GI phase, the p53-inducible subunit p53R2 provides dNTPs for BER. We previously reported that inhibition of RR by COH29 causes dNTP depletion in vivo (6).

COH29 may affect double stranded DNA break repair, as suggested by our data showing suppression of the HR complex protein Rad51. This is indicated by the observation that COH29 causes attenuation in the level of Rad51 protein intracellularly (FIG. 7A). In response to DNA damage, RAD51 translocates from the cytosol to the nucleus to form nucleofilaments on ssDNA, which is an essential step to promote the HR pathway (45,46). In untreated cells, the majority of Rad51 is expressed in the cytosol (FIG. 7B, upper panel). A significantly increased γ-H2AX expression in the nucleus paralleled with a dramatically decreased. Rad51 in response to exposure to COH29, suggests Rad51 may play a role in COH29-induced DSBs. This effect of COH29 on Rad51 is similar to that documented for HU, which is known to stall replication forks (47), with the important distinction that COH29 is 20-fold more potent than HU (6), and is not appreciably genotoxic (FIGS. 5A-5D).

In addition, COH29 also suppressed BRCA1, which is another important HR component. It has been reported that inhibition of PARP downregulates BRCA1 and RAD51 expression mediated by E2F4 and p230 (48). Developing inhibitors to interrupt the HR DNA repair machinery (51) has become attractive since elevated Rad51 expression has been observed in numerous types of cancer and is correlated with poor prognosis and drug resistance (52,53). It has been reported that increase of HR capacity by upregulating Rad51 expression level may cause resistance of cancer cells to PARP inhibitors (54). Even in BRCA1-defective cells, loss of 53BP1 can allow partial HR repair and mediate acquired resistance to PARP inhibitors (55). Inactivation of Rad51 functions via downregulating its expression level induced by COH29 may act as a potential therapy for cancers. Our data shows COH29 can interfere with the BER, NER, and HR repair pathways in cells, suggesting COH29 may target backup DNA repair resulting from genetic background or resistance to PARP inhibitors.

Increasing the potency of DNA damaging drugs through synthetic lethality or other means carries the risk of increasing the mutagenic potential of these drugs by suppressing the DNA repair capacity in vivo. In the case of dsB repair pathway, it was shown that inactivation of POLD1 (see above) causes colorectal adenomas and carcinomas (49). Polymorphism of RAD51 is associated with the onset of certain human cancer types (50). Nevertheless, the data herein has showed that COH29 treatment does not appear to render visible morphological anomalies during the embryonic development of zebrafish, unlike HU. The advances described here may lead to further improvement of the current strategy for treating human cancers. The effect of COH-29 on various human breast cancer cells is shown in Table 3.

TABLE 3

Effect of COH29, Cisplatin, and Paclitaxel on Breast Cancer Cell Lines.

| Cell Line | Description | COH29 $IC_{50}$ (μM) | Cisplatin $IC_{50}$ (μM) | Paclitaxel $IC_{50}$ (mM) |
| --- | --- | --- | --- | --- |
| HCC1937 | Triple negative | 7.25 ± 0.64 | 2.46 ± 0.11 | 4.04 ± 0.44 |
| HCC1937 + BRCA1 | Triple negative | 35.01 ± 3.63 | 2.93 ± 0.55 | 5.40 ± 0.07 |
| MCF-7 | ER+ PR(+) | 17.61 ± 1.54 | 12.12 ± 1.02 | 6.36 ± 1.11 |
| SKBR3 | ER− PR(−) HER2+ | 13.28 ± 0.03 | 0.99 ± 0.24 | 3.37 ± 0.08 |
| MDA-MB-231 | Triple negative | 9.70 ± 1.52 | 3.74 ± 0.21 | 2.01 ± 0.57 |

REFERENCES (1) Hehlmann R. Current CML therapy: progress and dilemma. *Leukemia.* 2003; 17:1010-2, (2) Shewach D S, Lawrence T S. Antimetabolite radiosensitizers. *Journal of clinical oncology: official journal of the American Society of Clinical Oncology,* 2007; 25:4043-50; (3) Reichard P. Ehrenberg A, Ribonucleotide reductase—a radical enzyme. *Science.* 1983; 221:514-9; (4) Xue L, Zhou B, Liu X, Qiu W, Jin Z, Yen Y. Wild-type p53 regulates human ribonucleotide reductase by protein-protein interaction with p53R2 as well as hRRM2 submits *Cancer Res.* 2003; 63:980-6; (5) Shao J, Zhou B, Zhu L, Qiu W, Yuan Y C, Xi B. et al. In vitro characterization of enzymatic properties and inhibition of the p53R2 subunit of human ribonucleotide reductase. *Cancer Res.* 2004; 64:1-6; (6) Young C W. Hodas S. Hydroxyurea: Inhibitory Effect on DNA Metabolism. *Science.* 1964; 146:1172-4; (7) Platt O S. Hydroxyurea for the treatment of sickle cell anemia. *The New England Journal of Medicine.* 2008; 358:1362-9; (8) Zhou B, Su L, Hu S, Hu W, Yip M L, Wu X et al. A small-molecule blocking ribonucleotide reductase holoenzyme formation inhibits cancer cell growth and overcomes drug resistance. *Cancer Res.* 2013; 73:6484-93; (9) Helleday T, Petermann E, Lundin C, Hodgson B, Sharma R A. DNA repair pathways as targets for cancer therapy. *Nature Reviews Cancer.* 2008; 8:193-204; (10) Balajee A S, Bohr V A. Genomic heterogeneity of nucleotide excision repair. *Gene.* 2000; 250:15-30; (11) Rouleau M, Patel A, Hendzel M J, Kaufmann S H, Poirier G G. PARP inhibition: PARP1 and beyond. *Nature Reviews Cancer.* 2010; 10:293-301; (12) Yelamos J, Farres J, Llacuna L, Ampurdanes C, Martin-Caballero J. PARP-1 and PARP-2: New players in tumour development. *American Journal of Cancer Research* 2011; 1:328-46; (13) D'Amours D, Desnoyers S, D'Silva I, Poirier G G. Poly(ADP-ribosyl)ation reactions in the regulation of nuclear functions. *The Biochemical Journal* 1999; 342 (Pt 2):249-68; (14) Simonin F, Menissier-de Murcia J, Poch O, Muller S, Gradwohl G, Molinete M, et al. Expression and site-directed mutagenesis of the catalytic domain of human poly(ADP-ribose)polymerase in *Escherichia coli*. Lysine 893 is critical for activity. *J Biol Chem.* 1990; 265:19249-56; (15) Gottipati P, Vischioni B, Schultz N, Solomons J, Bryant H E, Djureinovic T, et al. Poly(ADP-ribose) polymerase is hyperactivated in homologous recombination-defective cells. *Cancer Res.* 2010; 70:5389-98; (16) Moeller B J, Pasqualini R, Arap W. Targeting cancer-specific synthetic lethality in double-strand DNA break repair. *Cell Cycle* (Georgetown, Tex.). 2009; 8:1872-6; (17) Curtin N J. DNA repair dysregulation from cancer driver to therapeutic target. *Nature Reviews Cancer.* 2012; 12:801-17. (18) Miknyoczki S J, Jones-Rolin S, Pritchard S, Hunter K, Zhao H, Wan W, et al. Chemopotentiation of temozalomide, irinotecan, and cisplatin activity by CEP-6800, a poly(ADP-ribose) polymerase inhibitor. *Mol Cancer Ther.* 2003; 2:371-82; (19) Mukhopadhyay A, Plummer E R, Elattar A, Soohoo S, Uzri B, Quinn J E, et al. Clinicopathological features of homologous recombination-deficient epithelial ovarian cancers: sensitivity to PARP inhibitors, platinum, and survival. *Cancer Res.* 2012; 72:5675-82; (20) Sessa C. Update on PARP1 inhibitors in ovarian cancer. *Ann Oncol.* 2011; 72 Suppl 8; viii72-viii6; (21) Chung Y M, Park S H, Tsai W B, Wang S Y, Ikeda M A, Berek J S, et al. FOXO3 signalling links ATM to the p53 apoptotic pathway following DNA damage. *Nature Communications* 2012; 3:1000; (22) Tsai W B, Chung Y M. Takahashi Y, Xu Z, Hu M C. Functional interaction between FOXO3a and ATM regulates DNA damage response. *Nature Cell Biology* 2008; 10:460-7; (23) Bennardo N, Cheng A, Huang N, Stark J M. Alternative-NHEJ is a mechanistically distinct pathway of mammalian chromosome break repair. *PLoS Genetics.* 2008; 4:e1000110: (24) Un F, Qi C, Prosser M, Wang N, Zhou B, Bronner C, et al. Modulating ICBP90 to suppress human ribonucleotide reductase M2 induction restores sensitivity to hydroxyurea cytotoxicity. *Anticancer Res.* 2006; 26-2761-7: (25) Westerfield M. THE ZEBRAFISH BOOK: A GUIDE FOR THE LABORATORY USE OF ZEBRAFISH (BRACHYDANIO RERIO). Eugene, Oreg.: M. Westerfield: 1993; (26) Schneider C A, Rasband W S, Eliceiri K W. NIH Image to ImageJ: 25 years of image analysis. *Nature Methods.* 2012; 9:671-5; (27) Irizarry R A, Hobbs B, Collin F, Beazer-Barclay Y D, Antonellis K J, Scherf U, et al. Exploration, normalization, and summaries of high density oligonucleotide array probe level data. *Biostatistics.* 2003; 4:249-64; (28) Benjamini Y, Hochberg Y. CONTROLLING THE FALSE DISCOVERY RATE—A PRACTICAL AND POWERFUL APPROACH TO MULTIPLE TESTING. *J R Stat Soc Ser B-Methodol.* 1995; 57:289-300; (29) Ashburner M, Ball C A, Blake J A, Botstein D, Butler H, Cherry J M, et al. Gene ontology: tool for the unification of biology. The Gene Ontology Consortium. *Nature Genetics.* 2000; 25:25-9; (30) Ivshina A V, George J, Senko O, Mow B, Putti T C, Smeds J, et al. Genetic reclassification of histologic grade delineates new clinical subtypes of breast cancer. *Cancer Res.* 2006; 66:10292-301; (31) R Development Core Team. A Language and Environment for Statistical Computing. Vienna, Austria: R Foundation for Statistical Computing; 2013; (32) Wooster R, Weber B L. Breast and ovarian cancer. *The New England Journal of Medicine.* 2003; 348:2339-47; (33) DelloRusso C, Welcsh P L, Wang W, Garcia R L, King M C, Swisher E M. Functional characterization of a novel BRCA1-null ovarian cancer cell line in response to ionizing radiation. *Mol Cancer Res.* 2007; 5:35-45; (34) Tomlinson G E, Chen T T, Stastny V A, Virmani A K, Spillman M A, Tonk V, et al. Characterization of a breast cancer cell line derived from a germ-line BRCA1 mutation carrier. *Cancer Res.* 1998; 58:3237-42; (35) Anglesio M S, Arnold J M, George J, Tinker A V, Tothill R, Waddell N, et al. Mutation of ERDD2 provides a novel alternative mechanism, for the ubiquitous activation of RAS-MAPK in ovarian serous low malignant potential tumors. *Mol Cancer Res.* 2008; 6:1678-90; (36) Ziegler-Skylakakis K, Schwarz L R, Andrae U. Microsome- and hepatocyte-mediated mutagenicity of hydroxyurea and related aliphatic hydroxamic acids in V79 Chinese hamster cells. *Mutat Res.* 1985; 152:225-31; (37) Friedrisch J R, Pra D, Maluf S W, Bittar C M, Mergener M, Pollo T, et al. DNA damage in blood leukocytes of individuals with sickle cell disease treated with hydroxyurea. *Mutat Res.* 2008; 649: 213-20; (38) Houtgraaf J H, Versmissen J, van der Giessen W J. A concise review of DNA damage checkpoints and repair in mammalian cells. *Cardiovascular Revascularization Medicine: including Molecular Interventions.* 2006; 7:165-72; (39) Abbas T, Keaton M A, Dutta A. Genomic instability in cancer. *Cold Spring Harbor Perspectives in Biology.* 2013; 5:a012914; (40) Rabik C A, Dolan M E. Molecular mechanisms of resistance and toxicity associated with platinating agents. *Cancer Treatment Reviews.* 2007; 33:9-23, (41) Selvakumaran M, Pisarcik D A, Bao R, Yeung A T, Hamilton T C. Enhanced cisplatin cytotoxicity by disturbing the nucleotide excision repair pathway in ovarian cancer cell lines. *Cancer Res.* 2003; 63:1311-6; (42) Pendleton K P, Grandis J R. Cisplatin-Based Chemotherapy Options for Recurrent and/or Metastatic Squamous Cell Cancer of the Head and Neck. *Clinical Medicine Insights Therapeutics.* 2013; 2013; (43) Cheng H, Zhang Z, Borczuk A, Powell C A, Balajee A S, Lieberman H B, et al. PARP inhibition selectively increases sensitivity to cisplatin in ERCC1-low non-small cell lung cancer cells. *Carcinogenesis.* 2013; 34:739-49; (44) Tassone P, Di Martino M T, Ventura M, Pietragalia A, Cucinotto I, Calimeri T, et al. Loss of BRCA1 function increases the antitumor activity of cisplatin against human breast cancer xenografts in vivo. *Cancer Biology & Therapy.* 2009; 8:648-53; (45) Haaf T, Golub E I, Reddy G, Radding C M, Ward D C. Nuclear foci of mammalian Rad51 recombination protein in somatic cells after DNA damage and its localization in synaptonemal complexes. *Proc Natl Acad Sci USA.* 1995; 92:2298-302; (46) Baumann P, Benson F E, West S C. Human Rad51 protein promotes ATP-dependent homologous pairing and strand transfer reactions in vitro. *Cell.* 1996; 87:757-66, (47) Petermann E, Orta M L, Issaeva N, Schultz N, Helleday T. Hydroxyurea-stalled replication forks become progressively inactivated and require two different RAD51-mediated pathways for restart, and repair. *Molecular Cell.* 2010; 37:492-502; (48) Hegan D C, Lu Y, Stachelek G C, Crosby M E, Bindra R S, Glazer P M. Inhibition of poly(ADP-ribose) polymerase down-regulates BRCA1 and RAD51 in a pathway mediated by E2F4 and p130. *Proc Natl Acad Sci USA.*

2010; 107:2201-6; (49) Connell P P, Siddiqui N. Hoffman S, Kuang A, Khatipov E A, Weichselbaum R R, et al. A hot spot for RAD51C interactions revealed by a peptide that sensitizes cells to cisplatin. *Cancer Res.* 2004; 64:3002-5; (50) Sak A, Stueben G, Groneberg M, Bocker W, Stuschke M. Targeting of Rad51-dependent homologous recombination: implications for the radiation sensitivity of human lung cancer cell lines. *British Journal of Cancer.* 2005; 92:1089-97; (51) Zhu J, Zhou L, Wu G, Konig H, Lin X, Li G, et al. A novel small molecule RAD51 inactivator overcomes imatinib-resistance in chronic myeloid leukaemia. *EMBO Molecular Medicine.* 2013; 5:353-65; (52) Helleday T. Homologous recombination in cancer development, treatment and development of drug resistance. *Carcinogenesis.* 2010; 31:955-60; (53) Maacke H, Opitz S, Jost K, Hamdorf W, Henning W, Kruger S, et al. Over-expression of wild-type Rad51 correlates with histological grading of invasive ductal breast cancer *International Journal of Cancer.* 2000; 88:907-13; (54) Montoni A, Robu M, Pouliot E, Shah G M. Resistance to PARP1-Inhibitors in Cancer Therapy. *Frontiers in Pharmacology.* 2013; 4:18; (55) Aly A, Ganesan S. BRCA1, PARP, and 53BP1: conditional synthetic lethality and synthetic viability. *Journal of Molecular Cell Biology.* 2011; 3:66-74.

EMBODIMENTS

Embodiments of the subject matter disclosed herein include the following.

Embodiment 1

A method of treating cancer in a subject in need thereof, said method comprising administering an effective amount of COH29 (N-(4-(3,4-dihydroxyphenyl)-5-phenylthiazol-2-yl)-3,4-dihydroxybenzamide), wherein said subject is a BRCA1-defective subject a PARP1 inhibitor-resistant subject or a DNA-damaging anti-cancer agent resistant subject.

Embodiment 2

The method of embodiment 1, wherein said subject, is a breast cancer subject or an ovarian cancer subject.

Embodiment 3

The method of embodiment 1, wherein said administering inhibits DNA repair in said subject.

Embodiment 4

The method of embodiment 1, wherein said administering inhibits base excision repair (BER), nucleotide excision repair (NER) or double stranded DNA break repair in said subject.

Embodiment 5

The method of embodiment 1, wherein said administering increases γ-H2AX protein activity or expression in said subject.

Embodiment 6

The method of embodiment 1, wherein said administering lowers Rad51 protein activity or expression in said subject.

Embodiment 7

The method of embodiment 1, wherein said administering lowers BRCA1 protein activity or expression in said subject.

Embodiment 8

The method of embodiment 1, wherein said administering lowers PARP1 protein activity or expression in said subject.

Embodiment 9

A method of treating cancer in a subject in need thereof, said method comprising administering COH29 (N-(4-(3,4-dihydroxyphenyl)-5-phenylthiazol-2-yl)-3,4-dihydroxybenzamide): and a DNA-damaging anti-cancer agent in a combined synergistic amount.

Embodiment 10

The method of embodiment 9, wherein said subject is a BRCA1-defective subject or a PARP1 inhibitor-resistant subject.

Embodiment 11

The method of embodiment 10 wherein said subject is a breast cancer subject or an ovarian cancer subject.

Embodiment 12

The method of embodiment 9, wherein said DNA-damaging anti-cancer agent is a chemotherapeutic DNA-damaging agent.

Embodiment 13

The method of embodiment 12, wherein said chemotherapeutic DNA-damaging agent is an alkylating agent.

Embodiment 14

The method of embodiment 13, wherein said alkylating agent is an ethylenimine, methylmelamine, nitrosourea, nitrogen mustard, busulfan, cyclophosphamide, or procarbazine.

Embodiment 15

The method of embodiment 9, wherein said chemotherapeutic DNA-damaging agent is a Topoisomerase I agent, a Topoisomerase II agent, camptothecin, irinotecan, topotecan, cisplatin, carboplatin, oxaliplatin, adriamycin, doxorubicin, etoposide, a single-strand break agent, BCNU carmustine, CCNU, DTIC, cytoxan, ifosfamide, bleomycin, or mitomycin C.

Embodiment 16

The method of embodiment 9, wherein said DNA-damaging anti-cancer agent is cisplatin, gemcitabine or γ-irradiation.

What is claimed is:

1. A method of treating cancer in a subject in need thereof, said method comprising administering to said subject an effective amount of a compound having a structure:

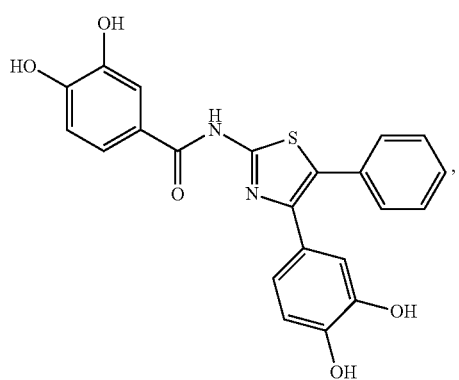

(COH29)

wherein said subject is a BRCA1-defective subject, a PARP1 inhibitor-resistant subject, or a DNA-damaging anti-cancer agent resistant subject.

2. The method of claim 1, wherein said subject is a breast cancer subject or an ovarian cancer subject.

3. The method of claim 1, wherein said administering inhibits DNA repair in said subject.

4. The method of claim 1, wherein said administering inhibits base excision repair (BER), nucleotide excision repair (NER) or double stranded DNA break repair in said subject.

5. The method of claim 1, wherein said administering increases y-H2AX protein activity or expression in said subject.

6. The method of claim 1, wherein said administering lowers Rad51 protein activity or expression in said subject.

7. The method of claim 1, wherein said administering lowers BRCA1 protein activity or expression in said subject.

8. The method of claim 1, wherein said administering lowers PARP1 protein activity or expression in said subject.

9. A method of treating cancer in a subject in need thereof, said method comprising administering to said subject a compound having a structure:

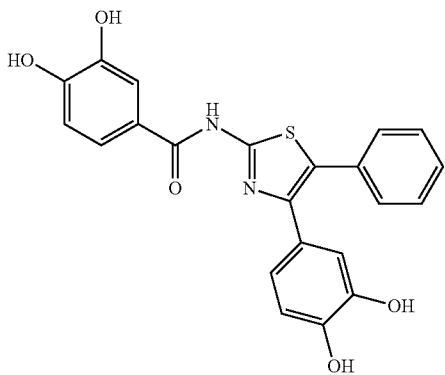

(COH29)

and a DNA-damaging anti-cancer agent in a combined synergistic amount.

10. The method of claim 9, wherein the subject is a BRCA1-defective subject or a PARP1 inhibitor-resistant subject.

11. The method of claim 10, wherein said subject is a breast cancer subject or an ovarian cancer subject.

12. The method of claim 9, wherein said DNA-damaging anti-cancer agent is a chemotherapeutic DNA-damaging agent.

13. The method of claim 12, wherein said chemotherapeutic DNA-damaging agent is an alkylating agent.

14. The method of claim 13, wherein said alkylating agent is an ethylenimine, methylmelamine, nitrosourea, nitrogen mustard, busulfan, cyclophosphamide, or procarbazine.

15. The method of claim 9, wherein said chemotherapeutic DNA-damaging agent is a Topoisomerase I agent, a Topoisomerase II agent, camptothecin, irinotecan, topotecan, cisplatin, carboplatin, oxaliplatin, adriamycin, doxorubicin, etoposide, a single-strand break agent, BCNU carmustine, CCNU, DTIC, cytoxan, ifosfamide, bleomycin, or mitomycin C.

16. The method of claim 9, wherein said chemotherapeutic DNA-damaging agent is cisplatin, gemcitabine or y-irradiation.

\* \* \* \* \*

UNITED STATES PATENT AND TRADEMARK OFFICE
CERTIFICATE OF CORRECTION

| | | |
|---|---|---|
| PATENT NO. | : 10,201,530 B2 | Page 1 of 1 |
| APPLICATION NO. | : 15/900677 | |
| DATED | : February 12, 2019 | |
| INVENTOR(S) | : Yun Yen | |

It is certified that error appears in the above-identified patent and that said Letters Patent is hereby corrected as shown below:

In the Specification

At Column 1, at Lines 21-25, delete "This invention was made with government support under grant number CA 127541, awarded by the National Institute of Cancer (NCI) and grant number P30CA033572 awarded by the National Institutes of Health (NIH). The government has certain rights in the invention." and insert -- This invention was made with government support under R01 CA127541 and P30 CA033572 awarded by the National Institutes of Health. The government has certain rights in the invention. --.

Signed and Sealed this
First Day of October, 2024

*Katherine Kelly Vidal*

Katherine Kelly Vidal
*Director of the United States Patent and Trademark Office*